United States Patent
Tilley et al.

(10) Patent No.: US 12,297,416 B2
(45) Date of Patent: *May 13, 2025

(54) SYSTEM AND METHOD FOR TRANSFERRING TISSUE

(71) Applicant: DEKA Products Limited Partnership, Manchester, NH (US)

(72) Inventors: Michael C. Tilley, Amherst, NH (US); Richard E. Andrews, Chula Vista, CA (US); Dane C. Fawkes, Amesbury, MA (US)

(73) Assignee: DEKA Products Limited Partneship, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/594,189

(22) Filed: Mar. 4, 2024

(65) Prior Publication Data

US 2024/0200011 A1   Jun. 20, 2024

Related U.S. Application Data

(63) Continuation of application No. 18/084,183, filed on Dec. 19, 2022, now Pat. No. 11,939,564, which is a
(Continued)

(51) Int. Cl.
*C12M 1/32* (2006.01)
*A61L 27/36* (2006.01)
(Continued)

(52) U.S. Cl.
CPC ......... *C12M 33/06* (2013.01); *A61L 27/3608* (2013.01); *A61L 27/3633* (2013.01);
(Continued)

(58) Field of Classification Search
CPC ......... B29C 64/10; B29C 64/20; B29C 64/30; C12M 33/00; C12M 33/06; C12M 21/08;
(Continued)

(56) References Cited

U.S. PATENT DOCUMENTS 5,156,053 A   10/1992   Shiraishi et al.
6,053,052 A   4/2000   Starastovic
(Continued)

FOREIGN PATENT DOCUMENTS

CA   2685964   5/2011
EP   2679669   1/2014
(Continued)

OTHER PUBLICATIONS

International Search Report, Int. App. # PCT/US2017/041791, mailed Dec. 15, 2017.
(Continued)

*Primary Examiner* — Nahida Sultana
(74) *Attorney, Agent, or Firm* — Mark E. Tetreault

(57) ABSTRACT

A transfer device designed to extract an amorphous or semi-solid structure, tissue, or construct from supporting media while maintaining the spatial integrity/organizational architecture thereof. The transfer device can include a controller, an actuator assembly, a plunger, and a needle. The controller can move the transfer device and the plunger independently.

6 Claims, 22 Drawing Sheets

Related U.S. Application Data continuation of application No. 17/140,459, filed on Jan. 4, 2021, now Pat. No. 11,530,380, which is a continuation of application No. 16/752,121, filed on Jan. 24, 2020, now Pat. No. 10,894,942, which is a continuation of application No. 16/117,225, filed on Aug. 30, 2018, now Pat. No. 10,570,362, which is a continuation of application No. 15/648,391, filed on Jul. 12, 2017, now Pat. No. 11,254,901.

(51) Int. Cl.
  *C12M 1/26* (2006.01)
  *C12M 3/00* (2006.01)
  *C12N 5/00* (2006.01)

(52) U.S. Cl.
  CPC ............ *C12M 21/08* (2013.01); *C12M 33/00* (2013.01); *C12N 5/0062* (2013.01); *C12N 2513/00* (2013.01)

(58) Field of Classification Search
  CPC .............. C12N 2513/00; C12N 5/0062; A61L 27/3608; A61L 27/3633
  See application file for complete search history.

(56) References Cited

U.S. PATENT DOCUMENTS

| | | |
|---|---|---|
| 6,103,528 A | 8/2000 | An et al. |
| 6,470,225 B1 | 10/2002 | Yutkowitz |
| 6,767,928 B1 | 7/2004 | Murphy et al. |
| 6,936,311 B2 | 8/2005 | Ringeisen et al. |
| 6,942,830 B2 | 9/2005 | Mulhaupt et al. |
| 6,986,739 B2 | 1/2006 | Warren et al. |
| 6,993,406 B1 | 1/2006 | Cesarano, III et al. |
| 7,051,654 B2 | 5/2006 | Boland et al. |
| 7,174,282 B2 | 2/2007 | Hollister et al. |
| 7,445,441 B2 | 11/2008 | West et al. |
| 7,509,183 B2 | 3/2009 | Lin et al. |
| 7,615,373 B2 | 11/2009 | Simpson et al. |
| 7,625,198 B2 | 12/2009 | Lipson et al. |
| 7,780,897 B2 | 8/2010 | Wicker et al. |
| 7,857,756 B2 | 12/2010 | Warren et al. |
| 8,143,055 B2 | 3/2012 | Forgacs et al. |
| 8,197,743 B2 | 6/2012 | Wicker et al. |
| 8,198,086 B2 | 6/2012 | Koga et al. |
| 8,241,905 B2 | 8/2012 | Forgacs et al. |
| 8,507,263 B2 | 8/2013 | Asnaghi et al. |
| 8,579,620 B2 | 11/2013 | Wu |
| 8,586,345 B2 | 11/2013 | Simpson et al. |
| 8,639,484 B2 | 1/2014 | Sun et al. |
| 8,691,274 B2 | 4/2014 | Xu et al. |
| 8,691,974 B2 | 4/2014 | Gatenholm et al. |
| 8,728,807 B2 | 5/2014 | Forgacs et al. |
| 8,747,880 B2 | 6/2014 | Forgacs et al. |
| 8,817,332 B2 | 8/2014 | Wu |
| 8,852,932 B2 | 10/2014 | Forgacs et al. |
| 8,931,880 B2 | 1/2015 | Murphy et al. |
| 9,005,972 B2 | 4/2015 | Xu et al. |
| 9,011,754 B2 | 4/2015 | Leong et al. |
| 9,039,998 B2 | 5/2015 | Guillemot et al. |
| 9,149,952 B2 | 10/2015 | Murphy et al. |
| 9,222,932 B2 | 12/2015 | Shepherd et al. |
| 9,227,339 B2 | 1/2016 | Murphy et al. |
| 9,242,031 B2 | 1/2016 | Bonassar et al. |
| 9,301,925 B2 | 4/2016 | Xu et al. |
| 9,303,245 B2 | 4/2016 | Rivron et al. |
| 9,315,043 B2 | 4/2016 | Murphy et al. |
| 9,442,105 B2 | 9/2016 | Shepherd et al. |
| 9,499,779 B2* | 11/2016 | Murphy ............... C12N 5/0062 |
| 9,556,415 B2 | 1/2017 | Forgacs et al. |
| 10,709,511 B2* | 7/2020 | Shelton, IV ........... A61B 34/35 |
| 2003/0083686 A1 | 5/2003 | Freeman et al. |
| 2003/0120183 A1 | 6/2003 | Simmons |
| 2004/0219668 A1 | 11/2004 | Frei |
| 2004/0253365 A1 | 12/2004 | Warren et al. |
| 2005/0079620 A1 | 4/2005 | Eberhard et al. |
| 2005/0230557 A1 | 10/2005 | Aghili |
| 2007/0106247 A1 | 5/2007 | Burnett et al. |
| 2007/0216334 A1 | 9/2007 | Jones |
| 2007/0227270 A1 | 10/2007 | Mennenga |
| 2008/0192104 A1 | 8/2008 | Nye et al. |
| 2008/0281533 A1 | 11/2008 | Galiot et al. |
| 2009/0142836 A1 | 6/2009 | Wang et al. |
| 2009/0208466 A1 | 8/2009 | Yoo et al. |
| 2010/0190254 A1 | 7/2010 | Chian et al. |
| 2011/0091926 A1 | 4/2011 | Frerich |
| 2011/0177590 A1 | 7/2011 | Clyne et al. |
| 2011/0319868 A1 | 12/2011 | Hiles et al. |
| 2012/0022441 A1 | 1/2012 | Kelly et al. |
| 2012/0116568 A1 | 5/2012 | Murphy et al. |
| 2013/0164339 A1 | 6/2013 | Murphy et al. |
| 2013/0177972 A1 | 7/2013 | Green et al. |
| 2013/0190210 A1 | 7/2013 | Murphy et al. |
| 2013/0238257 A1 | 9/2013 | Rajamani et al. |
| 2013/0304233 A1 | 11/2013 | Dean et al. |
| 2013/0345794 A1 | 12/2013 | Khatiwala et al. |
| 2014/0012225 A1 | 1/2014 | Yoo et al. |
| 2014/0052285 A1 | 2/2014 | Butcher et al. |
| 2014/0099709 A1 | 4/2014 | Presnell et al. |
| 2014/0120192 A1* | 5/2014 | Nakayama ............. C12M 33/04 425/446 |
| 2014/0228970 A1 | 8/2014 | Boland |
| 2014/0277679 A1 | 9/2014 | Weinberg et al. |
| 2014/0330418 A1 | 11/2014 | Wu |
| 2014/0330421 A1 | 11/2014 | Wu |
| 2015/0004273 A1 | 1/2015 | Forgacs et al. |
| 2015/0017140 A1 | 1/2015 | Bhatia et al. |
| 2015/0037445 A1 | 2/2015 | Murphy et al. |
| 2015/0084956 A1 | 3/2015 | Wu |
| 2015/0088291 A1 | 3/2015 | Wu |
| 2015/0105891 A1 | 4/2015 | Golway et al. |
| 2015/0119994 A1 | 4/2015 | Kang et al. |
| 2015/0224226 A1 | 8/2015 | Bhatia et al. |
| 2015/0282885 A1 | 10/2015 | King et al. |
| 2015/0307728 A1 | 10/2015 | Omenetto et al. |
| 2015/0335417 A1 | 11/2015 | Birla |
| 2015/0342720 A1 | 12/2015 | Koç et al. |
| 2015/0344828 A1 | 12/2015 | Forgacs et al. |
| 2015/0351896 A1 | 12/2015 | D'lima et al. |
| 2015/0376560 A1 | 12/2015 | Finlay et al. |
| 2016/0024461 A1 | 1/2016 | Sun et al. |
| 2016/0040132 A1 | 2/2016 | Sears et al. |
| 2016/0046832 A1 | 2/2016 | Wroblesky et al. |
| 2016/0083681 A1 | 3/2016 | Tavana et al. |
| 2016/0136895 A1 | 5/2016 | Beyer et al. |
| 2017/0073631 A1 | 3/2017 | Miyauchi |
| 2017/0198252 A1 | 7/2017 | Mironov et al. |
| 2017/0369827 A1* | 12/2017 | Langenfeld ........... A61L 27/222 |
| 2018/0079999 A1 | 3/2018 | Blanchard |
| 2018/0169947 A1 | 6/2018 | Jessen |
| 2018/0307207 A1 | 10/2018 | Atherton et al. |
| 2019/0162777 A1 | 5/2019 | Chiang |
| 2021/0000778 A1 | 1/2021 | Luther et al. |
| 2024/0238820 A1* | 7/2024 | Kim .................. B05C 11/1005 |

FOREIGN PATENT DOCUMENTS

| | | |
|---|---|---|
| EP | 3190171 | 7/2017 |
| GB | 2478801 | 5/2012 |
| WO | 2005081970 | 9/2005 |
| WO | 2008069759 | 6/2008 |
| WO | 2009154466 | 12/2009 |
| WO | 2011097330 | 8/2011 |
| WO | 2011107599 | 9/2011 |
| WO | 2011116125 | 9/2011 |
| WO | 2012122105 | 9/2012 |
| WO | 2013096741 | 6/2013 |
| WO | 2013158508 | 10/2013 |
| WO | 2013192290 | 12/2013 |
| WO | 2014039427 | 3/2014 |
| WO | 2014085725 | 6/2014 |
| WO | 2014110590 | 7/2014 |

(56) References Cited

FOREIGN PATENT DOCUMENTS

| | | |
|---|---|---|
| WO | 2014151921 | 9/2014 |
| WO | 2014194180 | 12/2014 |
| WO | 2014197999 | 12/2014 |
| WO | 2015054577 | 4/2015 |
| WO | 2015129881 | 9/2015 |
| WO | 2015158700 | 10/2015 |
| WO | 2015168528 | 11/2015 |
| WO | 2015173020 | 11/2015 |
| WO | 2015198025 | 12/2015 |
| WO | 2016012583 | 1/2016 |
| WO | 2016019078 | 2/2016 |
| WO | 2016022830 | 2/2016 |
| WO | 2016036275 | 3/2016 |

OTHER PUBLICATIONS

Leak Testing Case Studies: Small Medical Device Leak Test Machine, http://tqc.co.uk/leak-testing/leak-testing-small-medical-device-leak-test-machine.php, Jun. 29, 2017.

PCT/US2017/041791, Notification Concerning Transmittal of Copy of International Preliminary Report on Patentability (Chapter I of the Patent Cooperation Treaty), mailing date Jan. 24, 2019.

\* cited by examiner

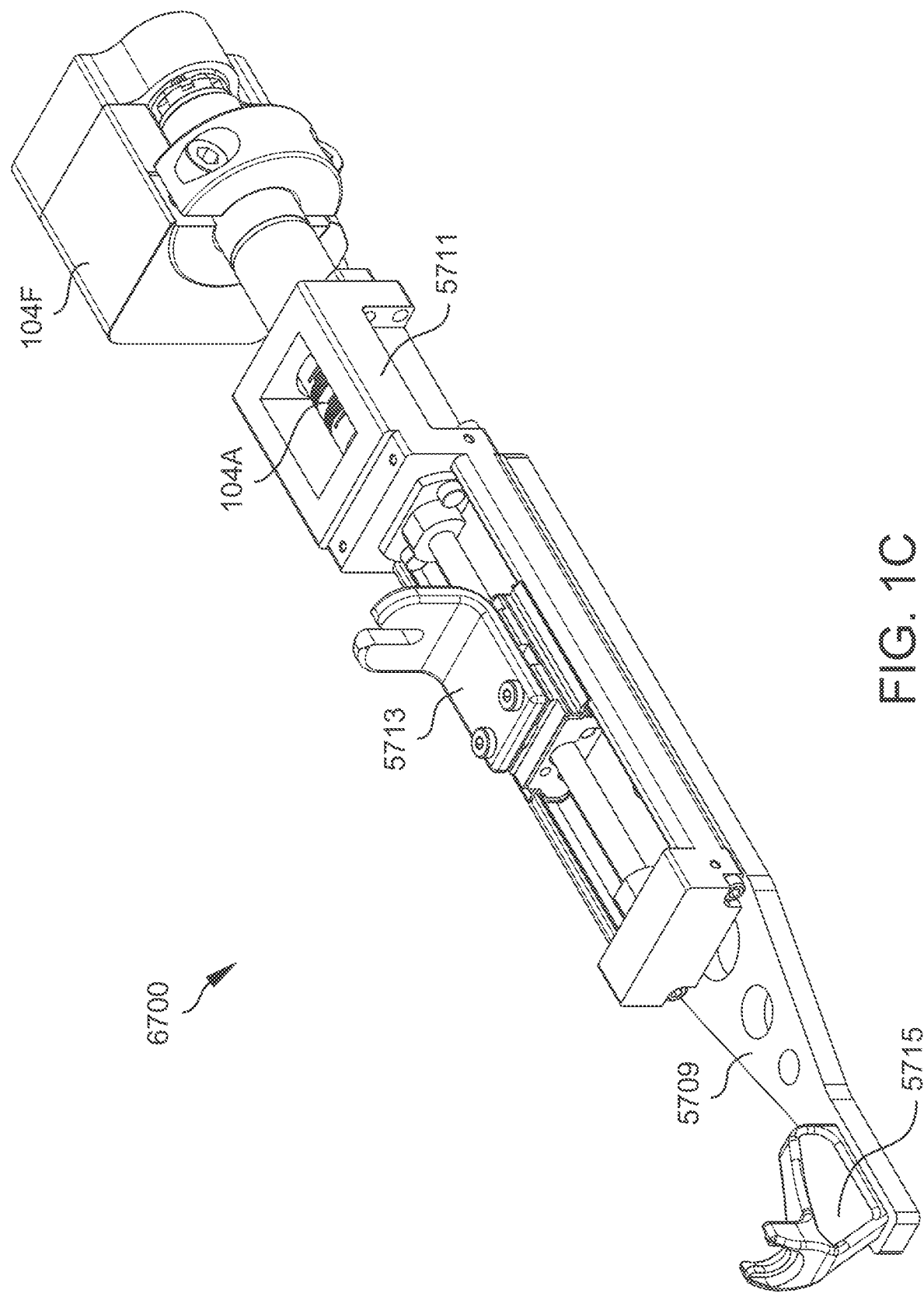

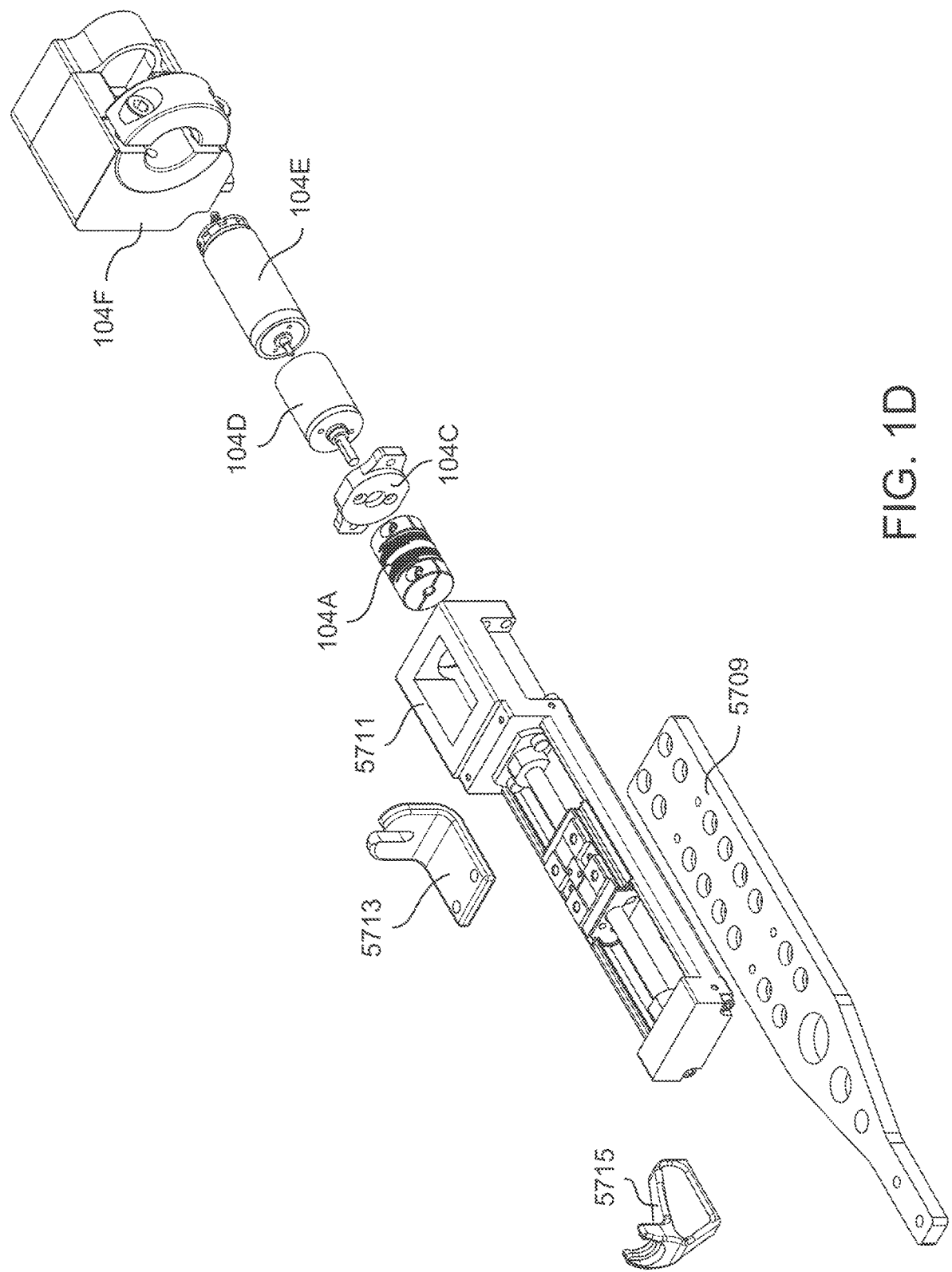

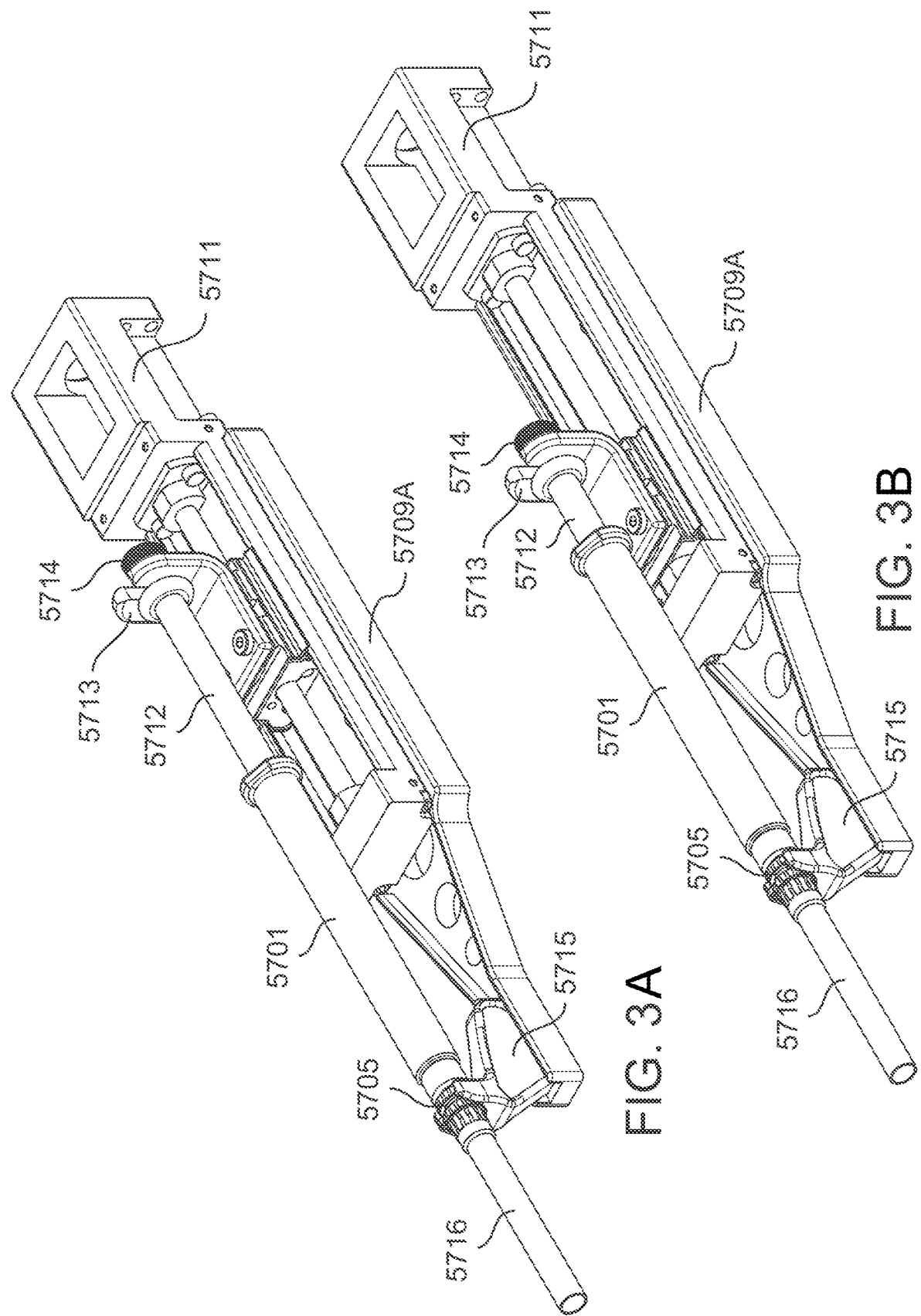

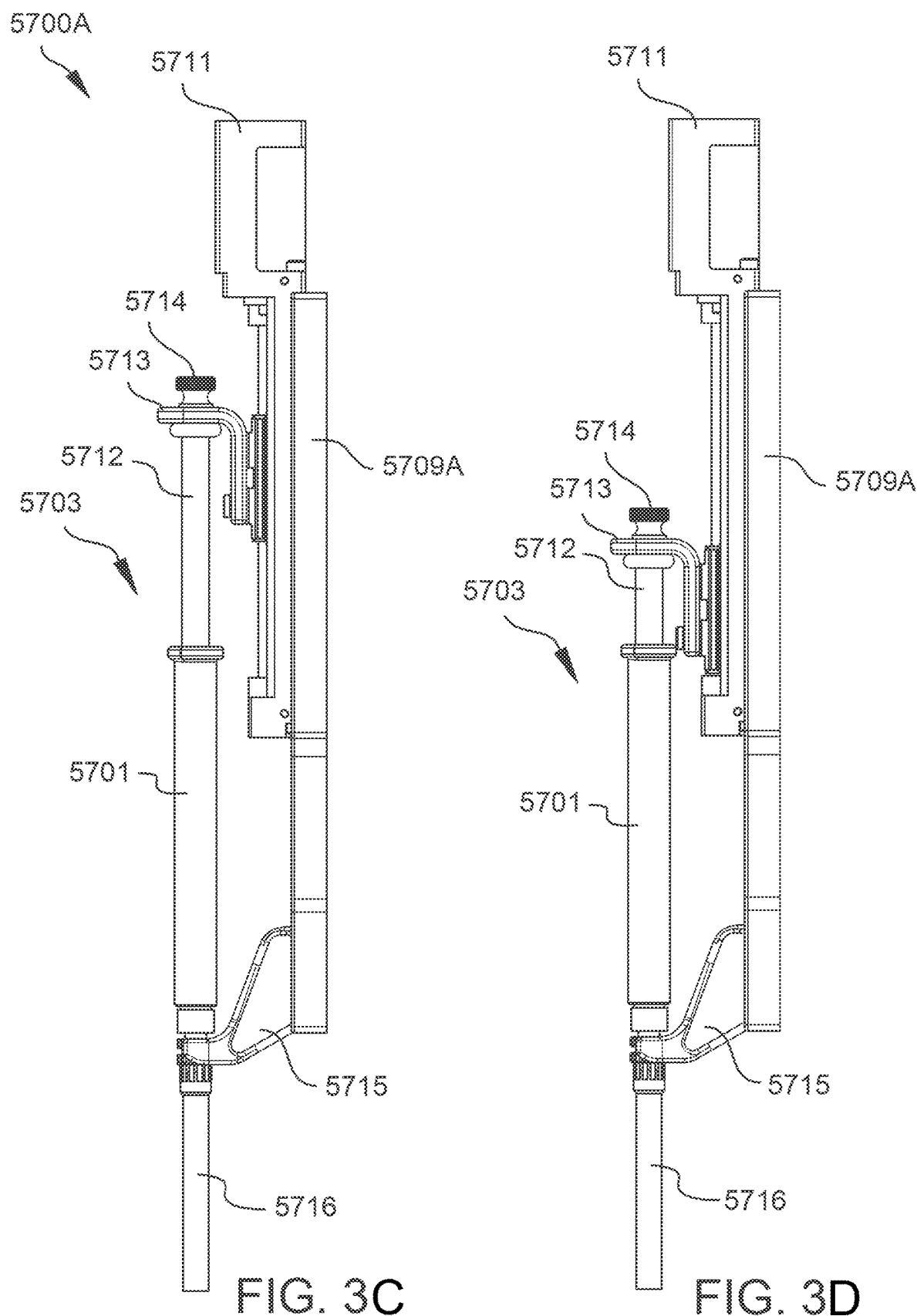

SYSTEM AND METHOD FOR TRANSFERRING TISSUE

CROSS REFERENCE TO RELATED APPLICATIONS

This application is a continuation of U.S. patent application Ser. No. 18/084,183, filed Dec. 19, 2022;
which is a continuation of U.S. patent application Ser. No. 17/140,459, filed Jan. 4, 2021, now U.S. Pat. No. 11,530,380;
which is a continuation of U.S. patent application Ser. No. 16/752,121, filed Jan. 24, 2020, now U.S. Pat. No. 10,894,942;
which is a continuation of U.S. patent application Ser. No. 16/117,225, filed Aug. 30, 2018;
which is a continuation-in-part of U.S. patent application Ser. No. 15/648,391, filed Jul. 12, 2017;
and claims the benefit of U.S. Provisional App. No. 62/553,355 filed Sep. 1, 2017, all of which are incorporated herein by reference in their entirety.

BACKGROUND

The present teachings relate generally to tissue engineering, and more specifically to systems and methods to enable the transfer of tissue from one medium to another.

In the course of development of viable bioprinted tissue, there can be a need to transplant a printed structure to, for example, but not limited to, address growth needs of the tissue. In some configurations, the process of bioprinting can involve depositing cell-laden bioinks into a medium. During the initial maturation phase, extracellular matrix (ECM) is secreted and organized by the cells. The cells can gain short range order and the first elements of structural integrity at this stage, and can, at initial printing and/or during the maturation phase, surround the medium. If the structure that is being formed requires movement to a location to continue growing, one issue can be the relative frailty of the tissue structure. What is needed is a means for moving the structure that can preserve the integrity of the structure.

SUMMARY

In some configurations, a means of transplanting the structure intact can include capturing a sacrificial layer external to the structure without disrupting the spatial distribution of the structure. If the medium is, for example, a hydrogel, allowable shear stresses can be relatively low, and the tolerance for compressive or tensile stress can be relatively higher than the allowable shear stresses. The tolerance for small amounts of compressive or tensile stress can be employed in the extraction process by capturing the sacrificial layer of the medium external to the structure. By doing so, the sacrificial layer may be subject to shear stresses, while the structure may experience a relatively small amount of transferred compressive strain.

The method of the present teachings for transferring a tissue structure using a transfer system can include, but is not limited to including depressing, by a pre-selected first amount and according to instructions by a controller part of the transfer system, a plunger part of the transfer system towards a needle part of the transfer system. The method can include moving the transfer device part of the transfer system, according to instructions by the controller, towards a first location of at least two transfer locations. The method can include inserting the needle into a first medium to a pre-selected depth and maintaining the first pre-selected distance between the plunger and the first medium, according to instructions by the controller. The first medium can be located at the first location, the first medium can include the tissue structure, and the inserted needle can surround the tissue structure and a sacrificial amount of the first medium. The method can include removing the needle, the plunger, the tissue structure, and the sacrificial amount a second pre-selected distance from the first medium while maintaining the first pre-selected distance between the plunger and the sacrificial amount, according to instructions from the controller. The method can include moving the transfer device, according to instructions from the controller, to a second location of the at least two transfer locations. The method can include inserting the needle, the tissue structure, and the sacrificial amount into the second medium to a second pre-selected depth in a second medium, and maintaining the first pre-selected distance between the plunger and the sacrificial amount, according to instructions from the controller. The method can include withdrawing the needle at a first rate and depressing the plunger at a second rate based on the first rate, according to instructions from the controller. The combination of the withdrawing and the depressing leaving the tissue structure and the sacrificial amount in the second medium.

The method can optionally include printing the tissue structure into the first medium. The first medium can optionally include a carbomer. The second medium can optionally include a carbomer. At least one of the at least two transfer locations can optionally include multiple well plates such as, for example, but not limited to, TRANSWELL® plates. At least one of the at least two transfer locations can optionally include bioreactors.

The transfer system of the present teachings for transferring a tissue structure from a first location of at least two locations to a second location of the at least two locations can include, but is not limited to including a transfer device including a needle and a plunger operably coupled with the needle, and a controller operably coupled with the transfer device and the plunger. The controller can execute instructions that can include, but are not limited to including, depressing, by a pre-selected first amount, the plunger towards the needle, and moving the transfer device towards the first location. The instructions can include inserting the needle into the first medium to a pre-selected depth and maintaining the first pre-selected distance between the plunger and the first medium. The first medium can be located at the first location, and can include the tissue structure. The inserted needle can surround the tissue structure and a sacrificial amount of the first medium. The instructions can include removing, by a second pre-selected distance from the first medium, the needle, the plunger, the tissue structure, and the sacrificial amount while maintaining the first pre-selected distance between the plunger and the sacrificial amount. The instructions can include moving the transfer device to the second location, and inserting, to a second pre-selected depth in a second medium, the needle, the tissue structure, and the sacrificial amount into the second medium and maintaining the first pre-selected distance between the plunger and the sacrificial amount. The instructions can include withdrawing the needle at a first rate and depressing the plunger at a second rate based on the first rate. The combination of the withdrawing and the depressing can leave the tissue structure and the sacrificial amount in the second medium.

BRIEF DESCRIPTION OF THE DRAWINGS

The present teachings will be more readily understood by reference to the following description, taken with the accompanying drawings, in which:

FIG. 1C is a schematic perspective diagram of the power transfer means of the tissue transfer system of the present teachings;

FIG. 1D is a schematic perspective exploded diagram of configuration of FIG. 1C;

FIGS. 3A-3D are schematic perspective diagrams of full and minimal plunger extension of the needle assembly of the tissue transfer system;

DETAILED DESCRIPTION

Figure 1:
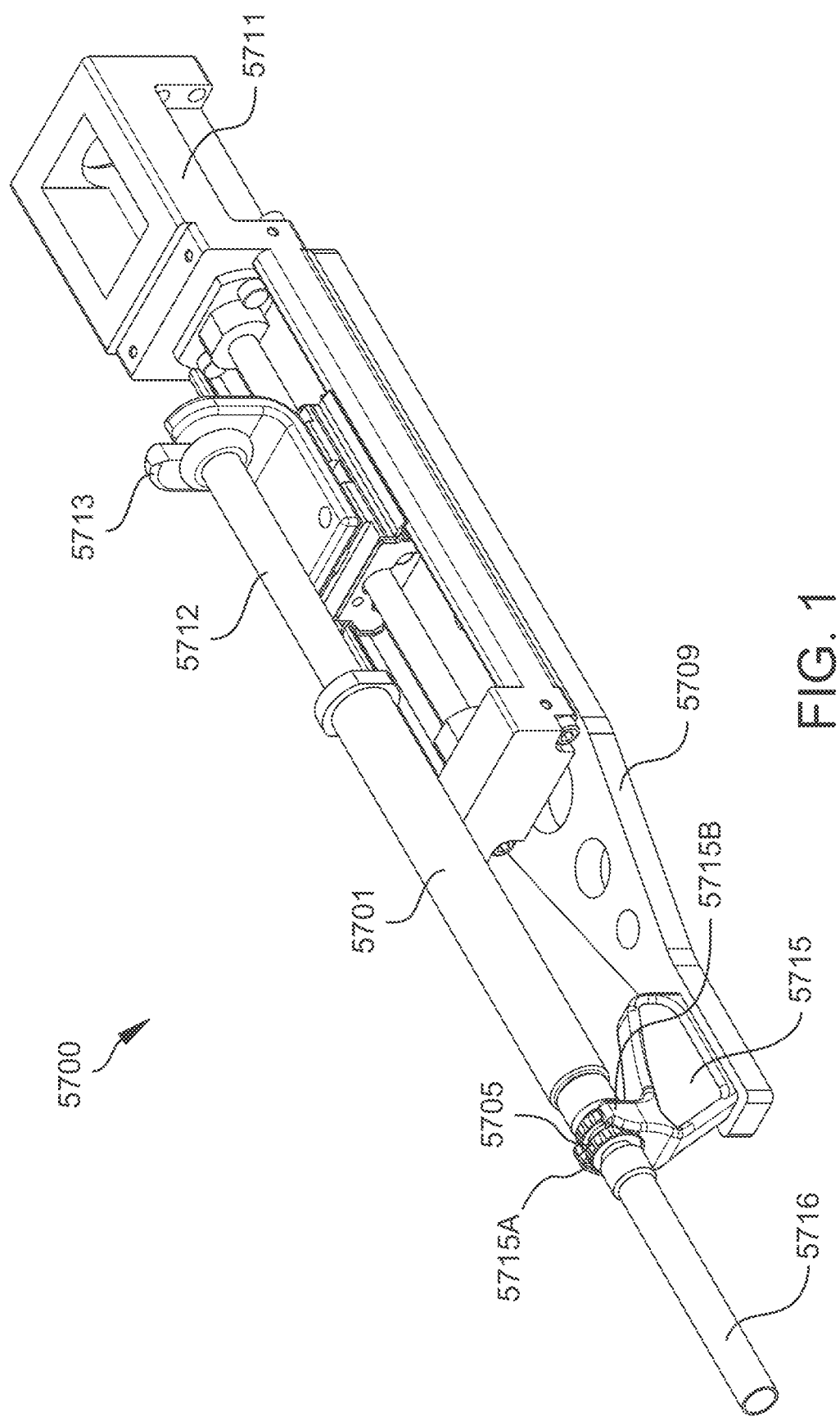
FIGS. 1, 1A, and 1B are schematic perspective diagrams of a first configuration of the tissue transfer system of the present teachings.
Figure 1A:
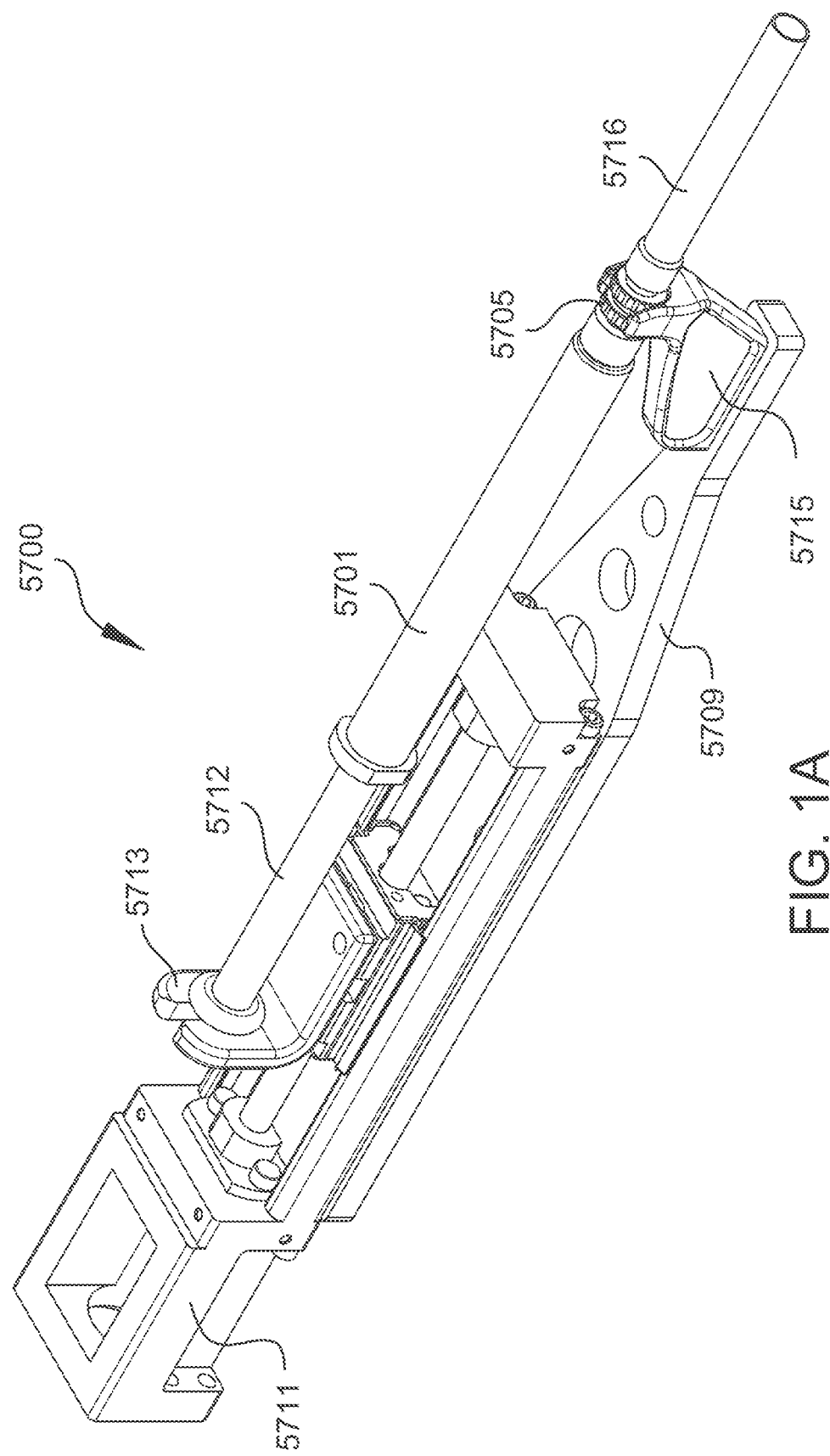
Figure 1B:
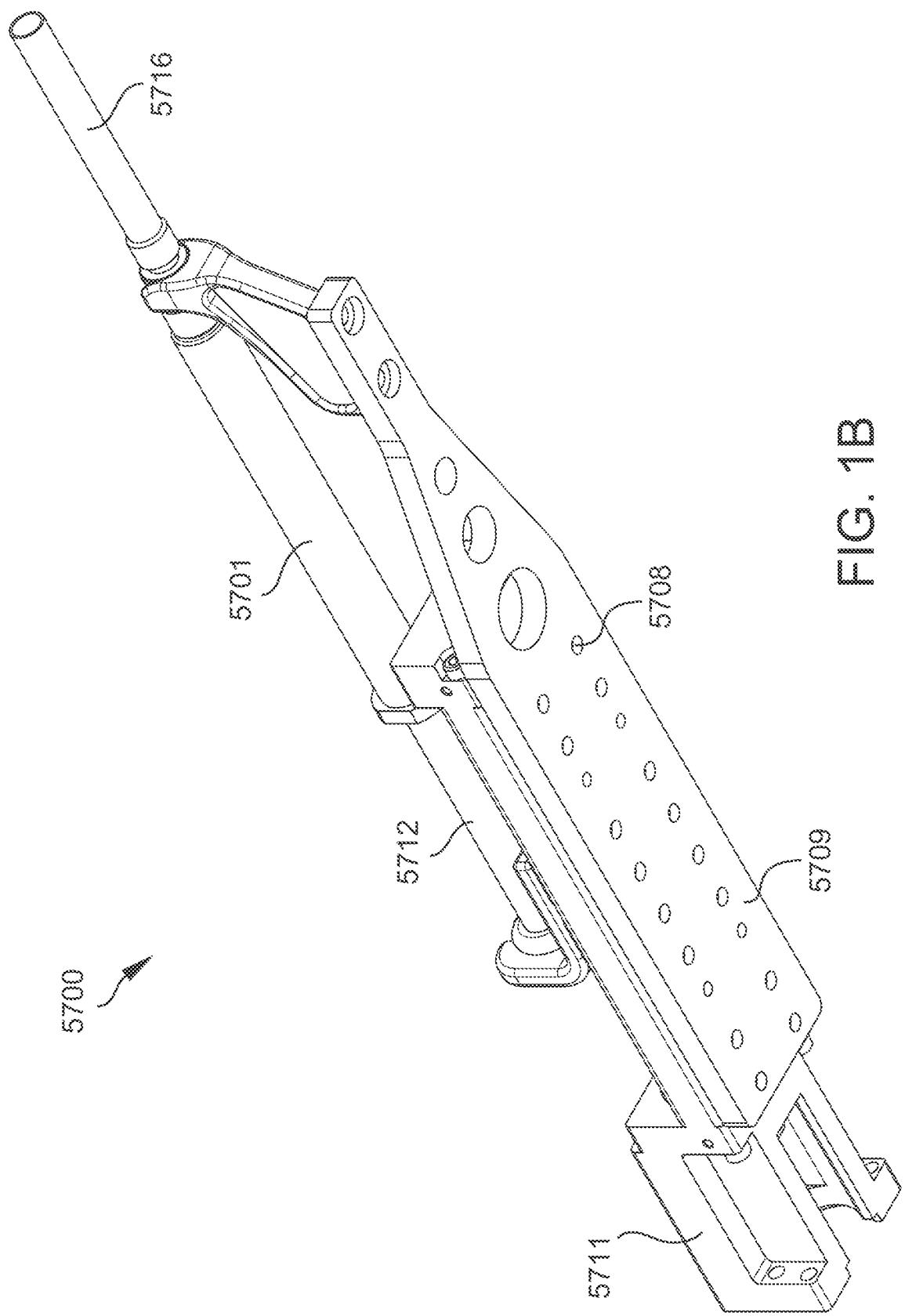
Figure 1E:
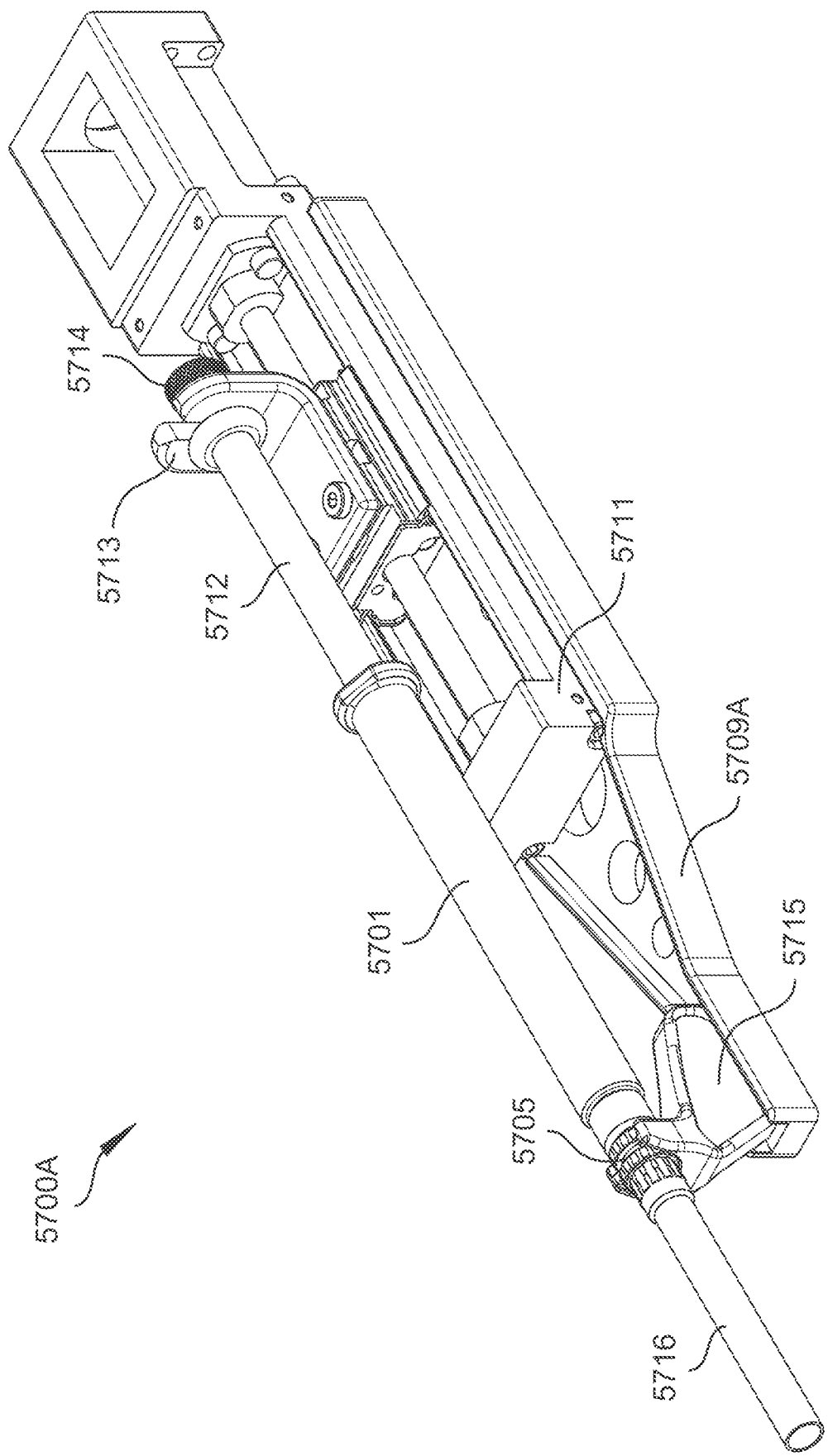
FIG. 1E is a schematic perspective diagram of a second configuration of the tissue transfer system of the present teachings.
Figure 2:
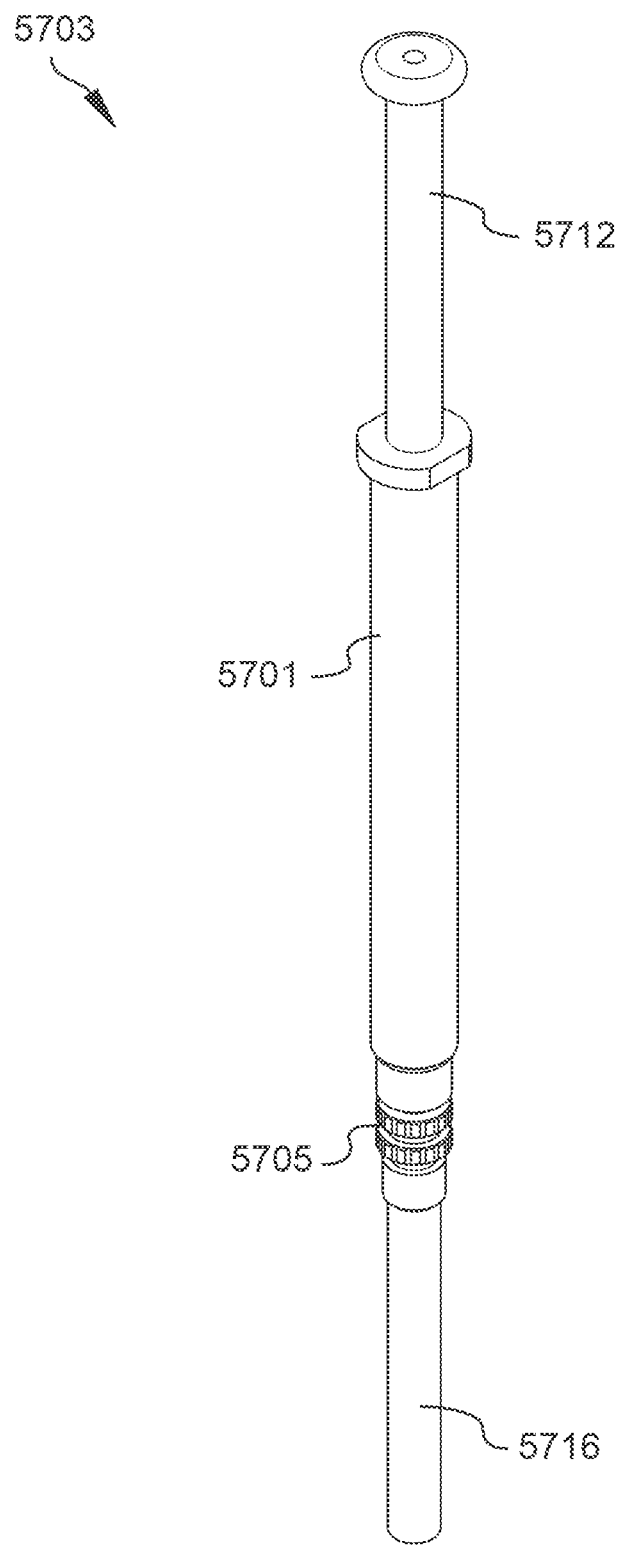
FIG. 2 is a schematic perspective diagram of the needle assembly of the tissue transfer system of the present teachings.
Figure 2A:
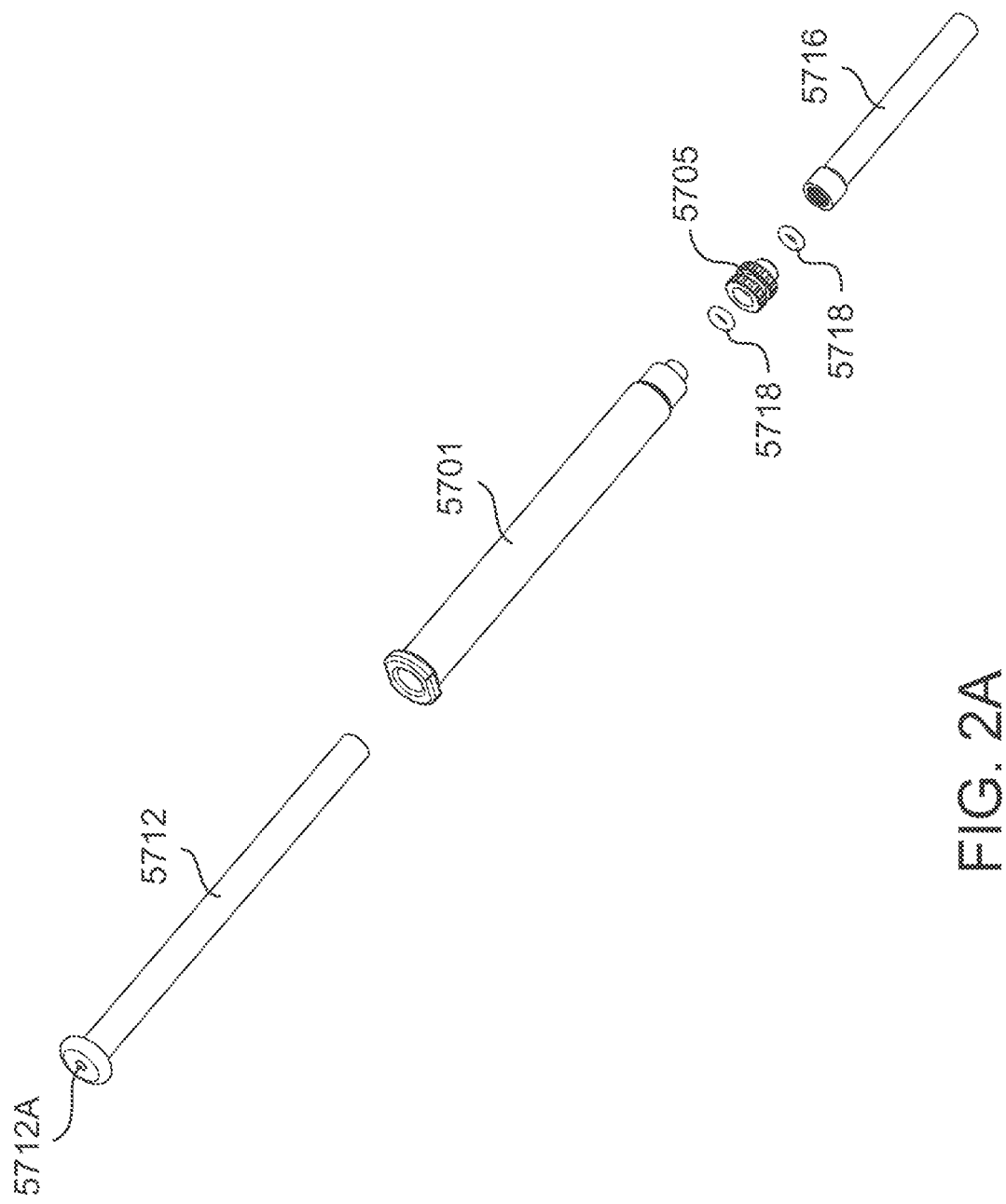
FIG. 2A is a schematic perspective exploded diagram of the needle assembly of FIG. 2.
Figure 2B:
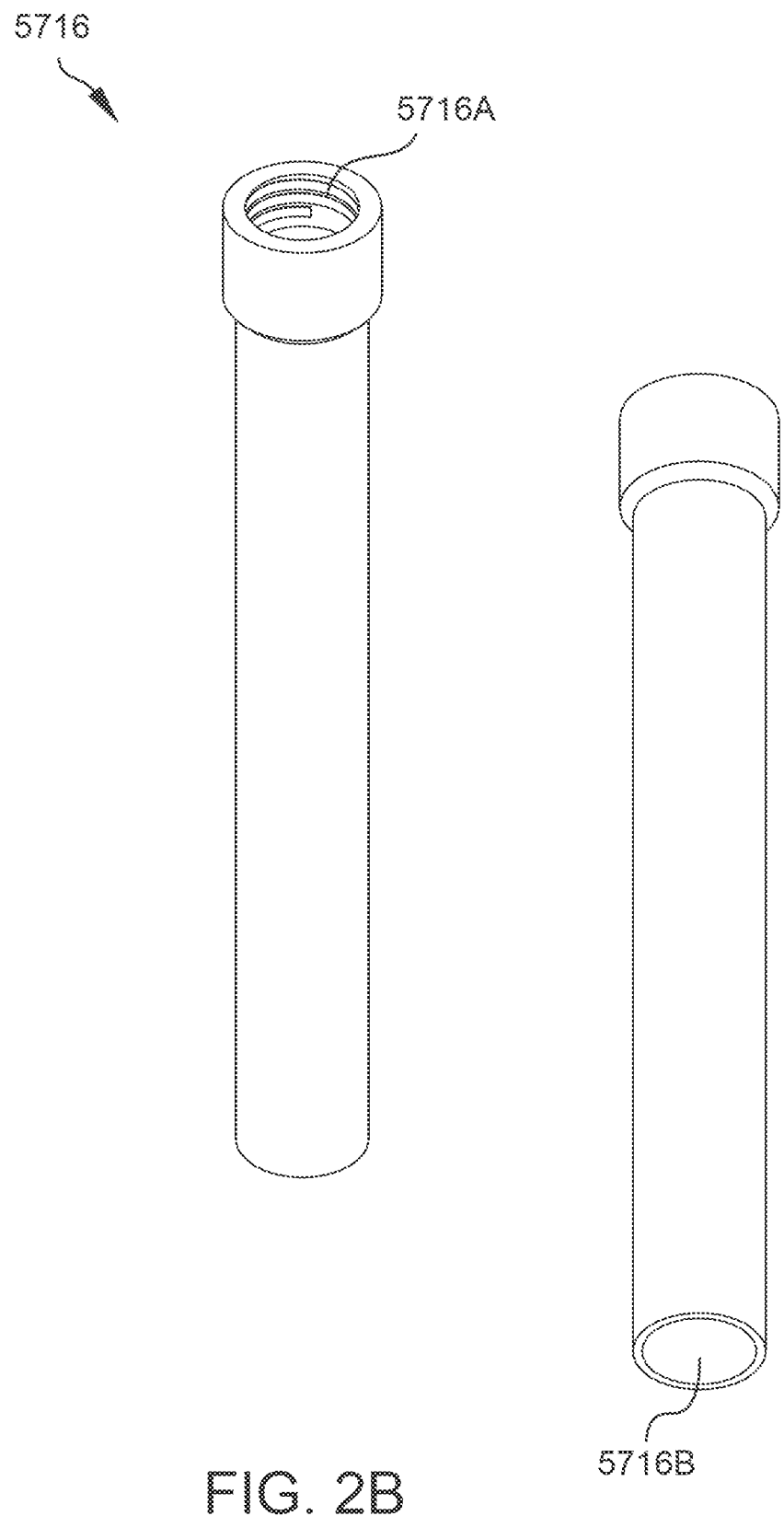
FIG. 2B is a schematic perspective diagram of the needle of the tissue transfer system of the present teachings.
Figure 2C:
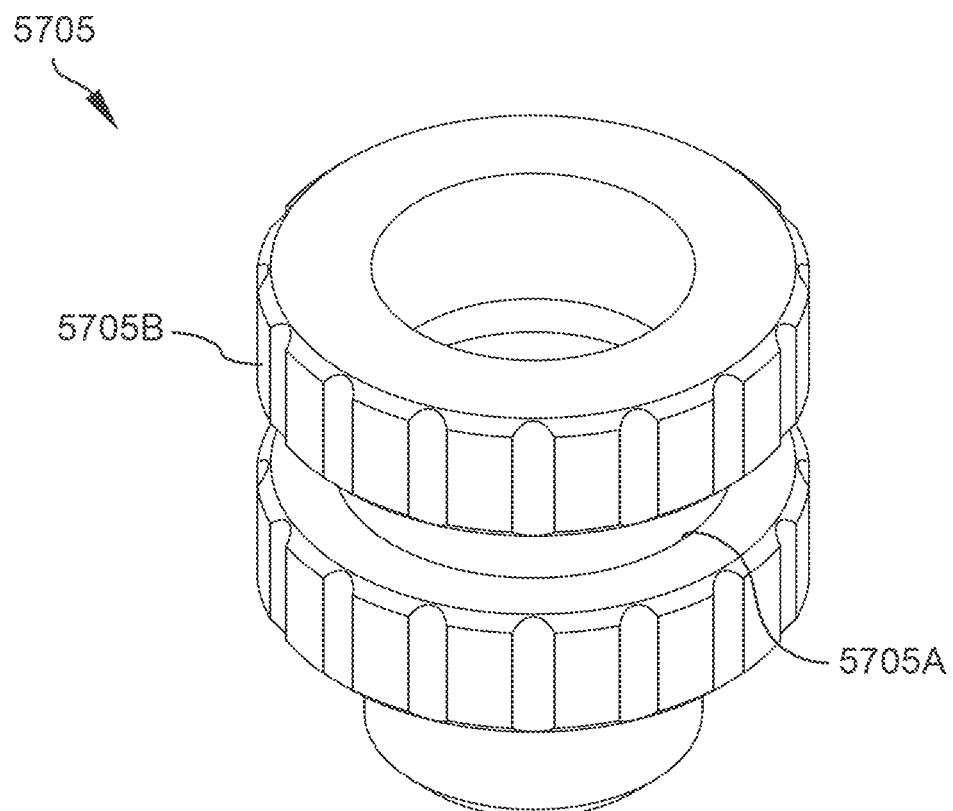
FIG. 2C is a schematic perspective diagram of the coupler hub of the tissue transfer system of the present teachings.
Figure 2C:
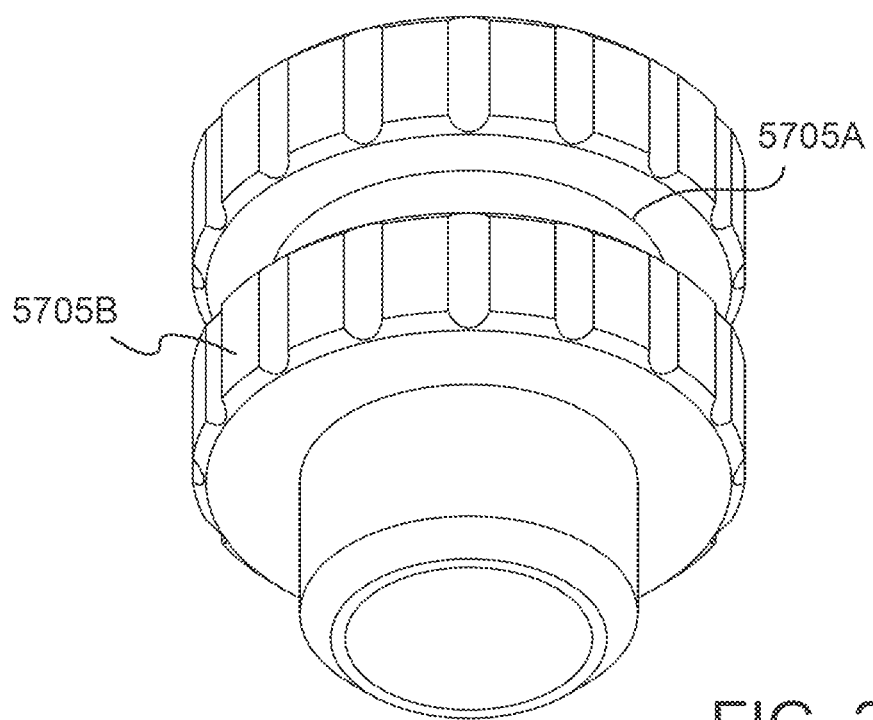

Referring now to FIGS. 1, 1A, and 1B, transfer device 5700 can move tissue structure from one location to another while maintaining the integrity of the tissue structure. A controller such as, for example, but not limited to, the controller described in the printer system of U.S. patent application Ser. No. 15/648,391, filed Jul. 12, 2017, entitled System and Method for Printing Tissue, incorporated herein by reference in its entirety, can be programmed to move transfer device 5700 to the location of the tissue, withdraw the tissue, move transfer device 5700 to a transfer location, and deposit the tissue intact into the transfer location. In some configurations, the controller can be programmed to withdraw tissue from a first growth area, and deposit the tissue into a second growth area. The controller can access a computer-aided design of the growth areas and can receive commands to move the tissue to various growth areas, depending upon the application. Transfer device 5700 can include, but is not limited to including, back plate 5709 that can include fastening cavities 5708 (FIG. 1B) for mounting hub retention yoke 5715 and linear actuator 5711. Hub retention yoke 5715 can include ears 5715A/5715B that can surround coupler hub 5705 (FIG. 2C). Plunger 5712 can include cavity 5712A (FIG. 2A) such as, for example, a threaded cavity, that can accommodate plunger mounting fixture such as, for example, but not limited to, thumb screw 5714 (FIG. 1E). The plunger mounting fixture can rest securely in plunger mount 5713. Plunger mount 5713 can be operably coupled with linear actuator 5711, which can enable movement of plunger 5712.

Referring now to FIGS. 1C and 1D, in some configurations, transfer device 6700 can include linear actuator 5711 that can be driven by motor 104E that can be coupled with linear actuator 5711 through clamp-on helical flexible shaft coupling 104A, linear drive adapter 104D, and motor mount 104C. Motor 104E can be mounted in junction housing 104F. In some configurations, clamp-on helical flexible shaft coupling 104A, a commercially-available product, can transmit torque through co-axial shafts that are separately housed/constrained.

Figure 1F:
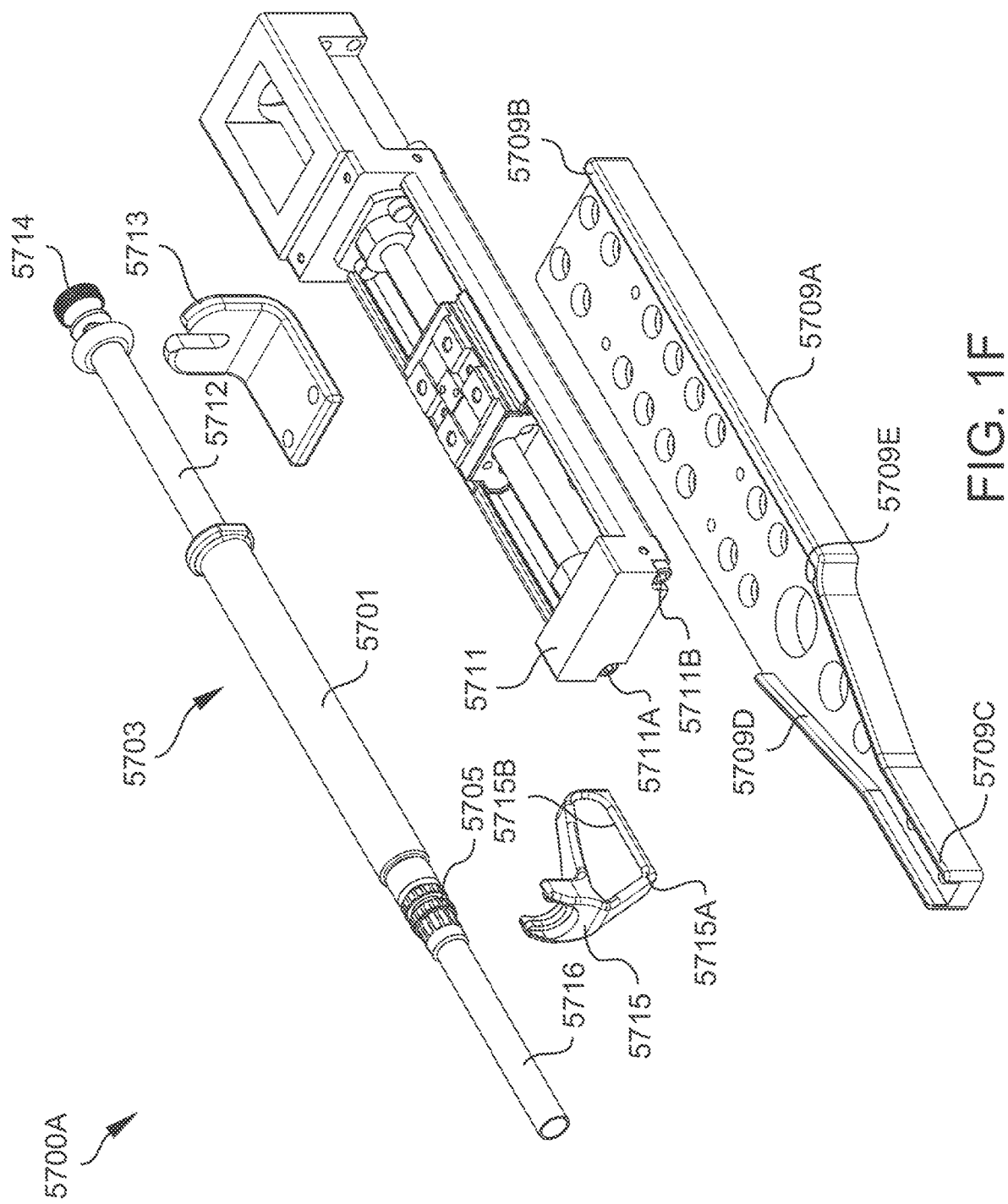
FIG. 1F is a schematic perspective exploded diagram of configuration of FIG. 1E.

Referring to FIGS. 1E and 1F, second configuration transfer device 5700A can include second configuration back plate 5709A. Second configuration back plate 5709A can include edging ribs 5709B that can provide alignment features for mounting linear actuator 5711 and hub retention yoke 5715. Edging ribs 5709B can provide raised features 5709C against which hub retention yoke mount edges 5715A/5715B can rest. Edging ribs 5709B can provide actuator stops 5709D/5709E upon which actuator corners 5711A/5711B can rest.

Referring now to FIGS. 2 and 2A-2C, coupler hub 5705 (FIG. 2C) can maintain the position of barrel 5701 and needle 5716 as needle 5716 withdraws and deposits the tissue. Coupler hub 5705 (FIG. 2C) can be operably coupled with needle 5716. In some configurations, needle threaded cavity 5716A (FIG. 2B) can enable operable coupling between coupler hub 5705 (FIG. 2C) and needle 5716. Coupler hub 5705 (FIG. 2C) can be surrounded by o-rings 5718 (FIG. 2A) that can maintain a fluid-resistant seal throughout syringe pump 5703 (FIG. 1F). Coupler hub 5705 (FIG. 2C) can include cavity 5705A, surrounded by placement rings 5705B, into which features of hub retention yoke 5715 (FIG. 1F) can rest to securely maintain the position of coupler hub 5705 and thus needle 5716. Needle bore 5716B (FIG. 2B) can be sized according to the size of the structure being transferred. One kind of structure that can be transferred is a vessel that can take the shape of a thin walled right cylinder. The vessel can be deposited, for example, printed, into a first medium in the growth area, and the interior of the cylinder can be filled with the medium.

Referring primarily to FIGS. 3A, 3B, 3C, 3D, and 3E, in operation, a controller can (a) force 5801 (FIG. 3B) plunger 5712 into (see FIGS. 3B and 3D) syringe barrel 5701, (b) direct transfer device 5700 (FIG. 3A) to move 5803 (FIG. 3D) to a first growth area, (c) direct linear actuator 5711 to a pre-selected displacement of plunger 5712, and (d) direct 5805 (FIG. 3D) needle 5716 to a pre-selected depth into the growth media, maintaining plunger 5712 at a pre-selected distance above the growth medium.

Continuing to refer primarily to FIGS. 3A-3E, when 5807 needle 5716 has reached the pre-selected depth, the controller can direct linear actuator 5711 to reverse direction 5809 of needle 5716, and to move 5811 needle 5716 and plunger 5712 from the first growth area, maintaining plunger 5712 at the pre-selected distance from the growth medium. As the controller directs linear actuator 5711 to withdraw needle 5716 and plunger 5712, the tissue and media from the first growth area that are within needle 5716 are withdrawn within the bore of needle 5716. Capturing a sacrificial layer while preserving the integrity of the tissue structure can be achieved by controlling syringe pump 5703 (FIG. 1F) fitted with needle 5716 to draw in or expel a volume linked to the motion of syringe pump 5703 (FIG. 1F). By correlating the volume displaced or vacated by the movement of syringe pump 5703 (FIG. 1F) to the exact volume sampled or dispensed by syringe pump 5703 (FIG. 1F), the tissue structure can be both removed from a first growth area and dispensed into second growth area. Bore 5716B (FIG. 2B) can be chosen to be larger than the tissue structure by a predetermined amount. The chosen size of bore 5716B (FIG. 2B) can allow for the capture of a sacrificial layer in addition to the tissue structure during extraction. The extracted structure within a larger 'plug' can concentrate the shear forces on the sacrificial layer, and can maintain the integrity of the tissue structure. When 5813 needle 5716 reaches a desired height, for example, the height at which there is no longer contact between needle 5716 and the first growth area, the controller can direct 5815 transfer device 5700 to a second growth area. The controller can direct needle 5716 and plunger 5712 to move 5817 into the second area, maintaining the pre-selected distance between plunger 5712 and the extracted tissue structure and sacrificial medium. When 5819 needle 5716 has reached a desired depth within the second area, the controller can direct needle 5716 to withdraw 5821 from the second growth area. At the same time, the controller can direct linear actuator 5711 to depress 5823 plunger 5712 at a rate relative to the movement rate of needle 5716 so that the depth of needle 5716, that includes the tissue structure and the sacrificial medium, steadily decreases. When 5825 needle 5716 reaches a desired height, the controller can direct needle 5716 and plunger 5712 to stop 5827 moving.

Figure 3E:
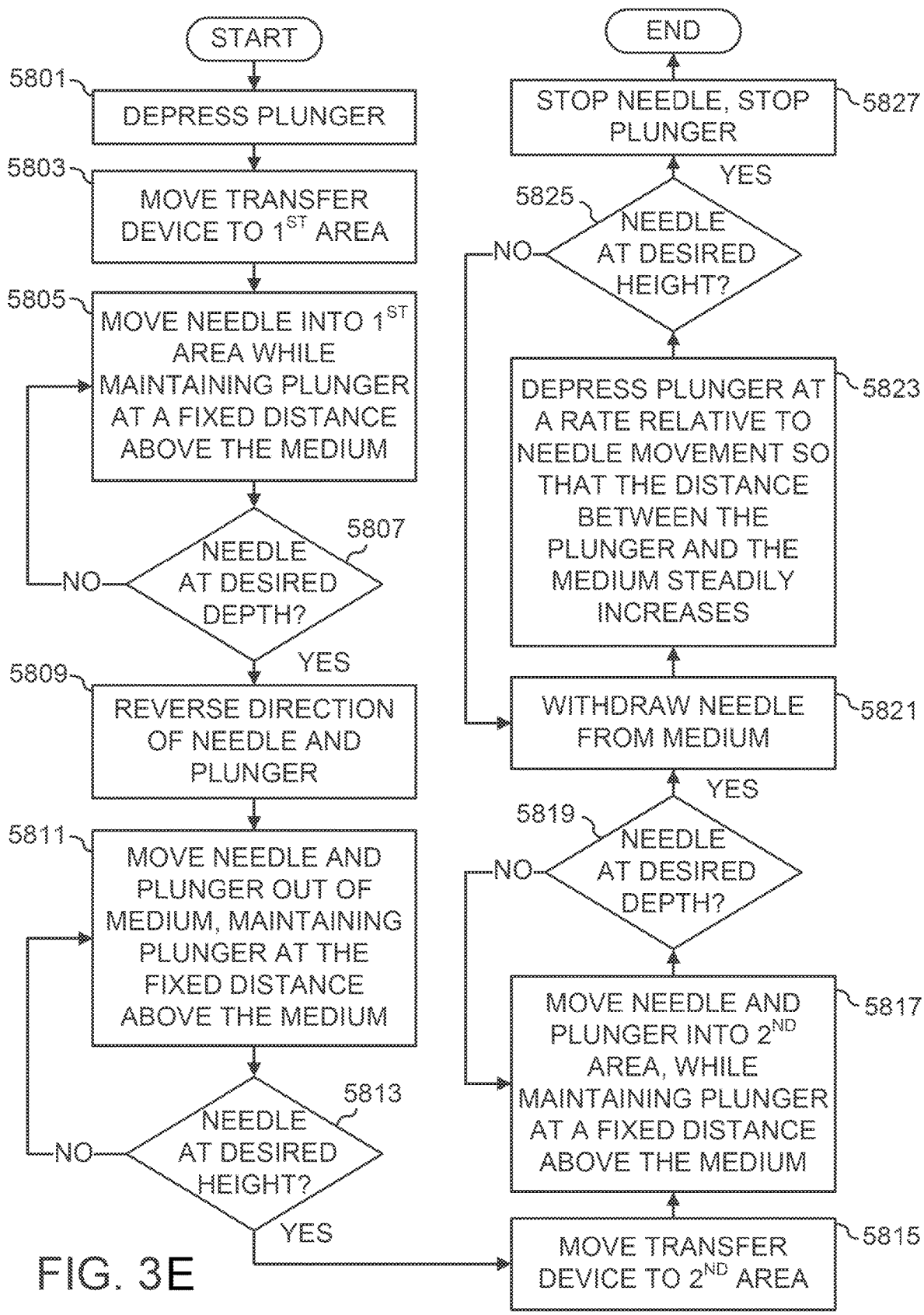
FIG. 3E is a schematic block diagram of the method of tissue transfer of the present teachings.
Figure 3F:
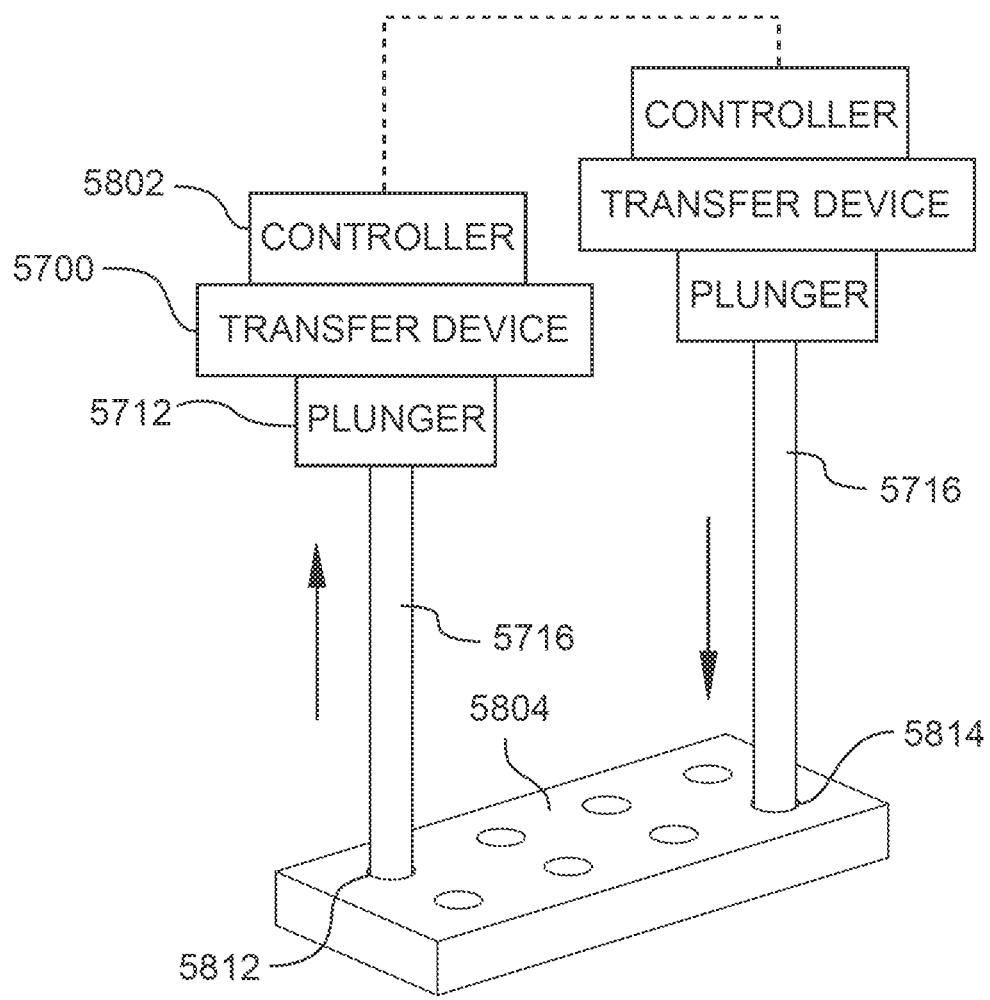
FIGS. 3F and 3G are schematic pictorial block diagrams of the method of the tissue transfer of the present teachings.

Referring now to FIG. 3F, controller 5802 can direct transfer device 5700 to move to first well 5812 in multiple well plate 5804, and to move from first well 5812 to second well 5814 in multiple well plate 5804. Controller 5802 can direct transfer device 5700 to position needle 5716 within first well 5812, and withdraw needle 5716 from first well 5812 to capture a tissue structure along with sacrificial medium as described herein. Controller 5802 can direct transfer device 5700 to move to second well 5814, and can direct transfer device 5700 to position needle within second well 5814. Simultaneously, controller can direct plunger 5712 to depress, forcing the tissue structure and sacrificial medium to exit needle 5716 and remain within second well 5814.

Figure 3G:
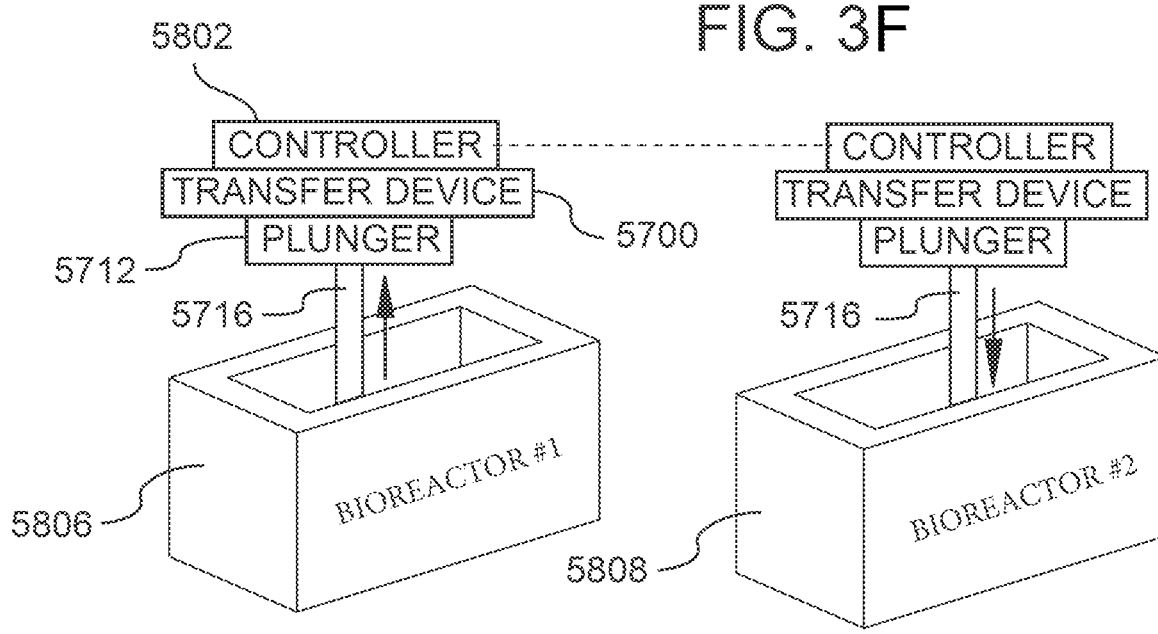

Referring now to FIG. 3G, controller 5802 can direct transfer device 5700 to move to first bioreactor 5806, and to move from first bioreactor 5806 to second bioreactor 5808. Controller 5802 can direct transfer device 5700 to position needle 5716 within first bioreactor 5806, and withdraw needle 5716 from first bioreactor 5806 to capture a tissue structure along with sacrificial medium as described herein. Controller 5802 can direct transfer device 5700 to move to second bioreactor 5808, and can direct transfer device 5700 to position needle within second bioreactor 5808. Simultaneously, controller can direct plunger 5712 to depress, forcing the tissue structure and sacrificial medium to exit needle 5716 and remain within second bioreactor 5808.

Figure 4A:
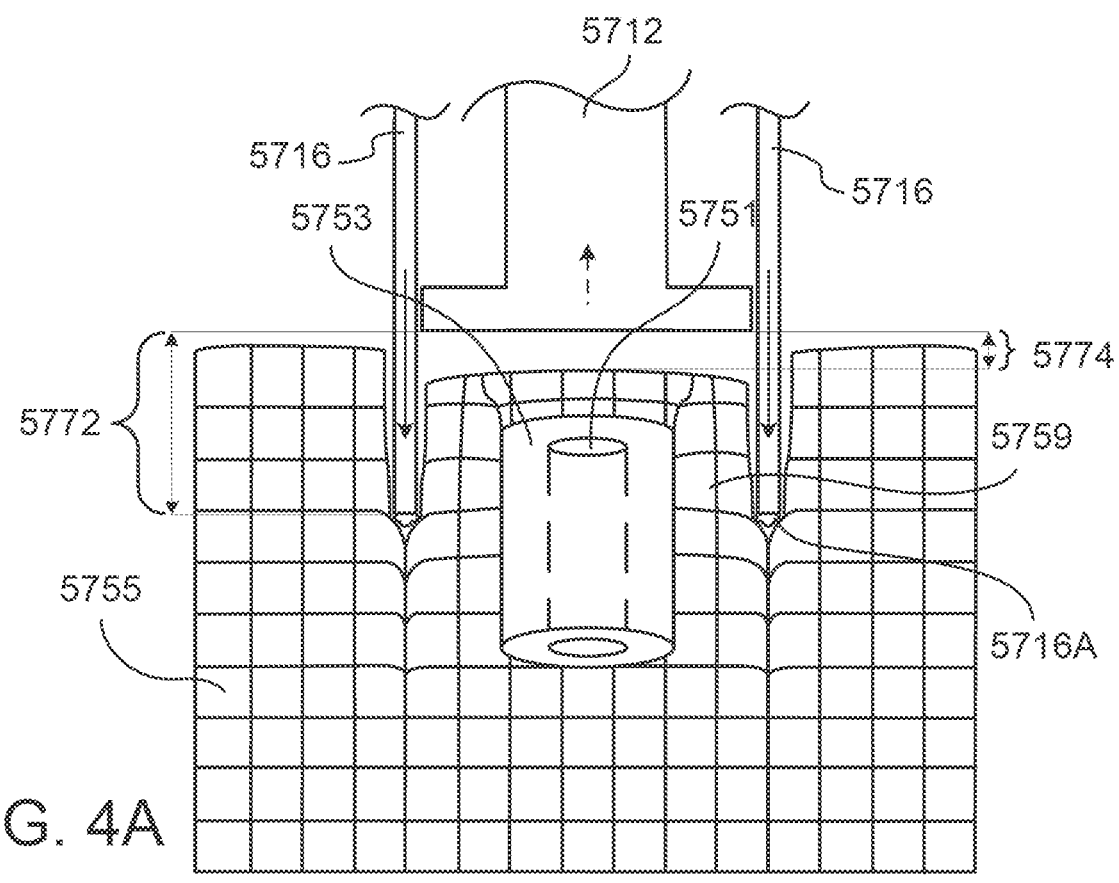
FIGS. 4A-4M are schematic pictorial diagrams of tissue transfer of the present teachings.
Figure 4B:
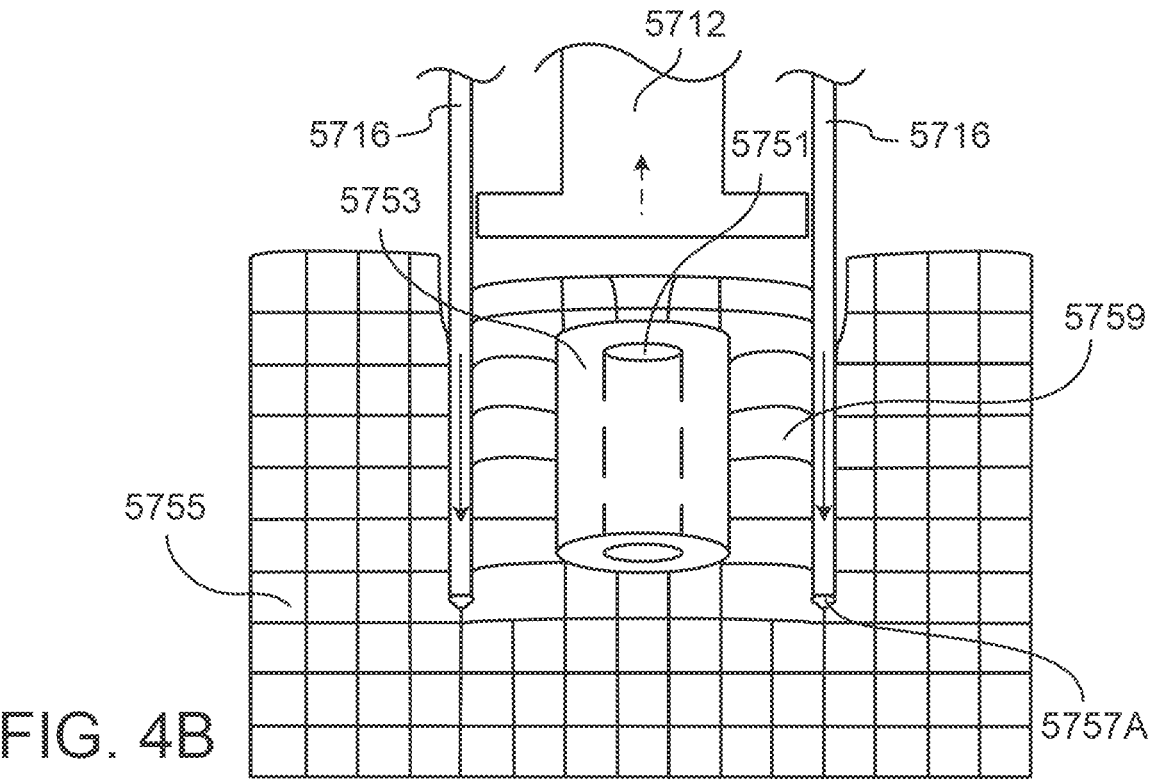
Figure 4C:
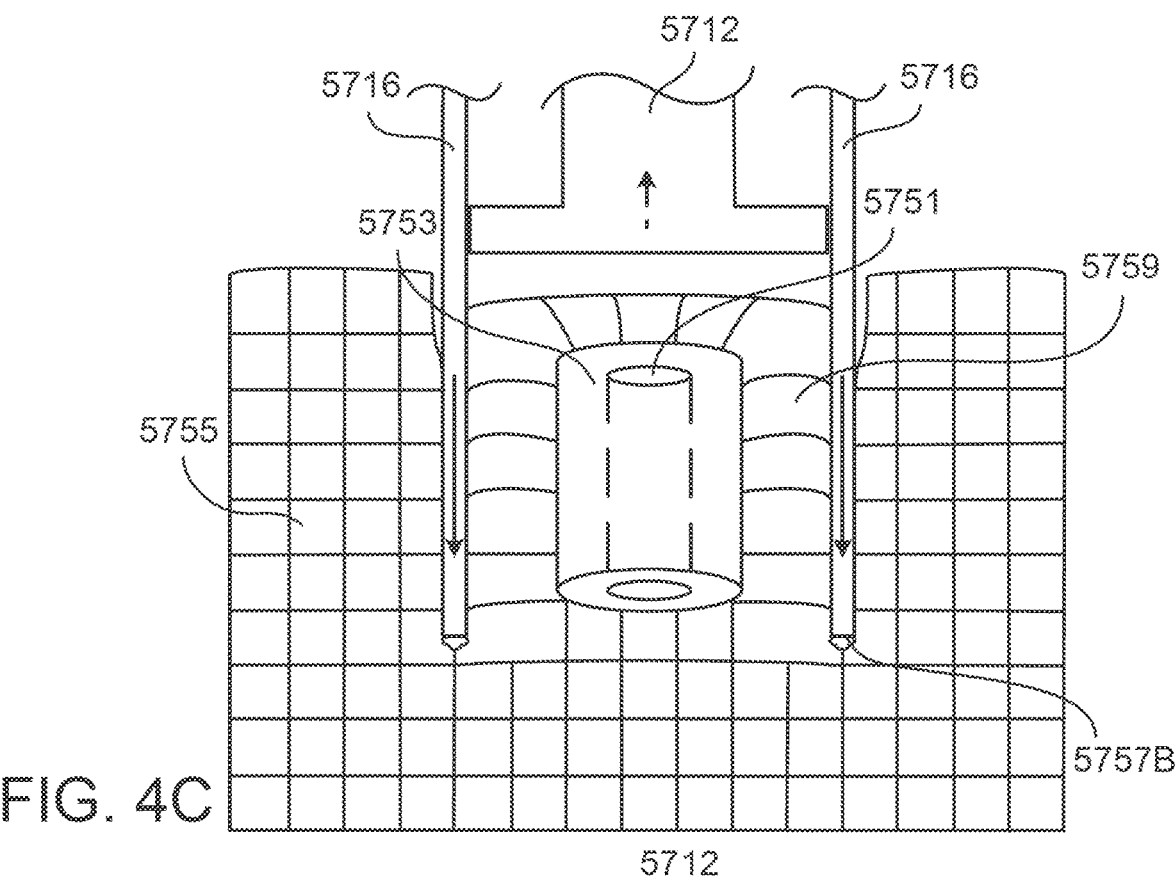
Figure 4D:
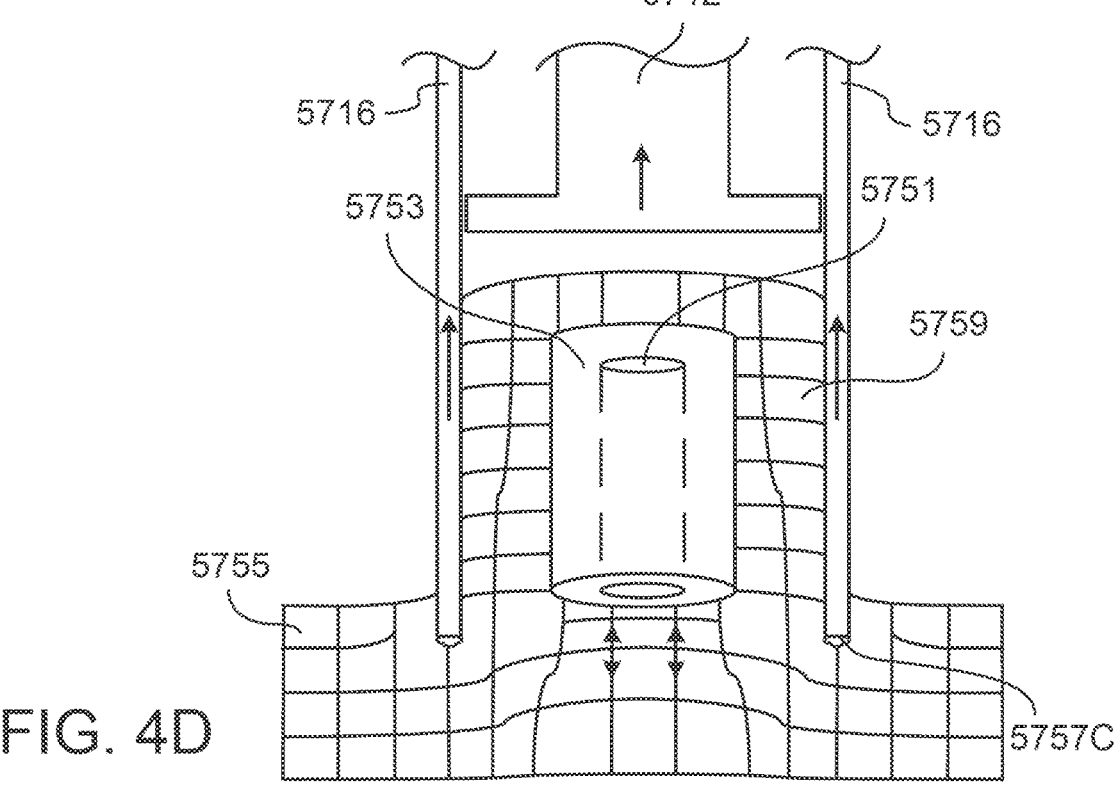
Figure 4E:
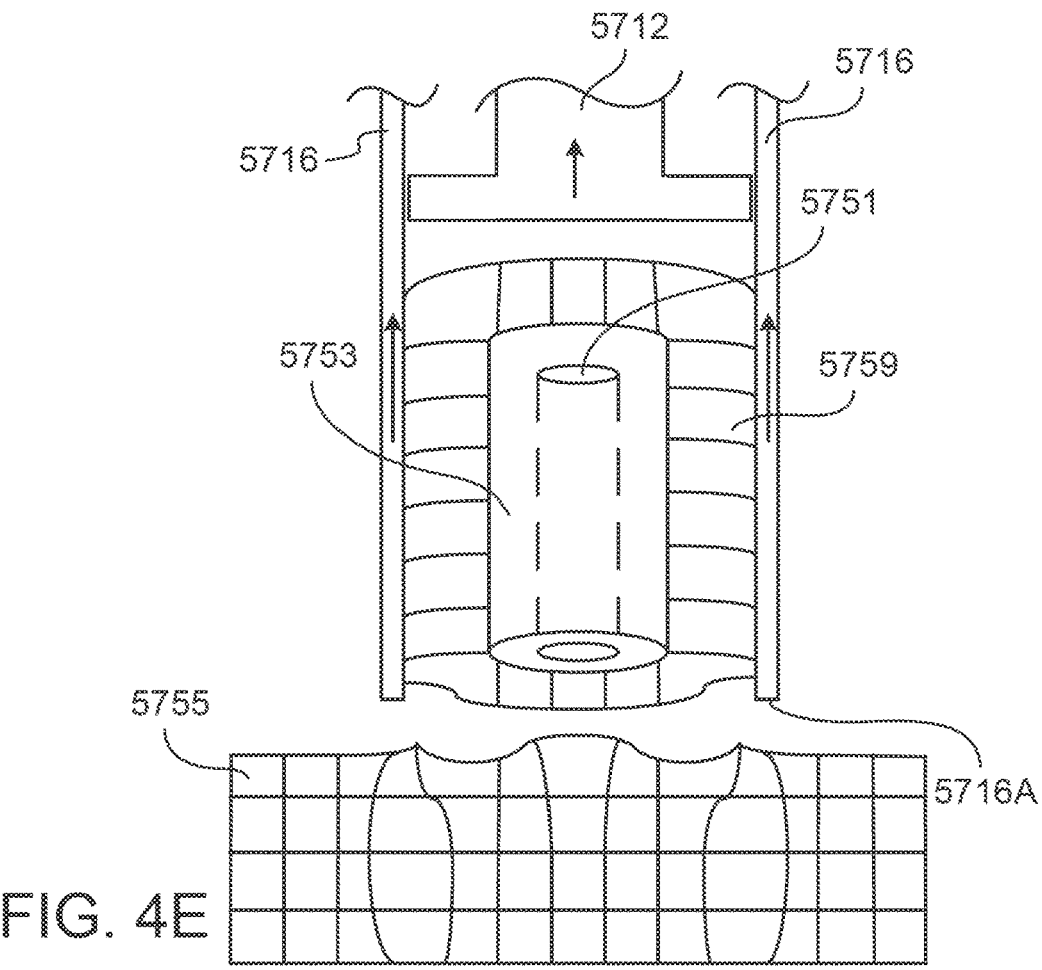
Figure 4F:
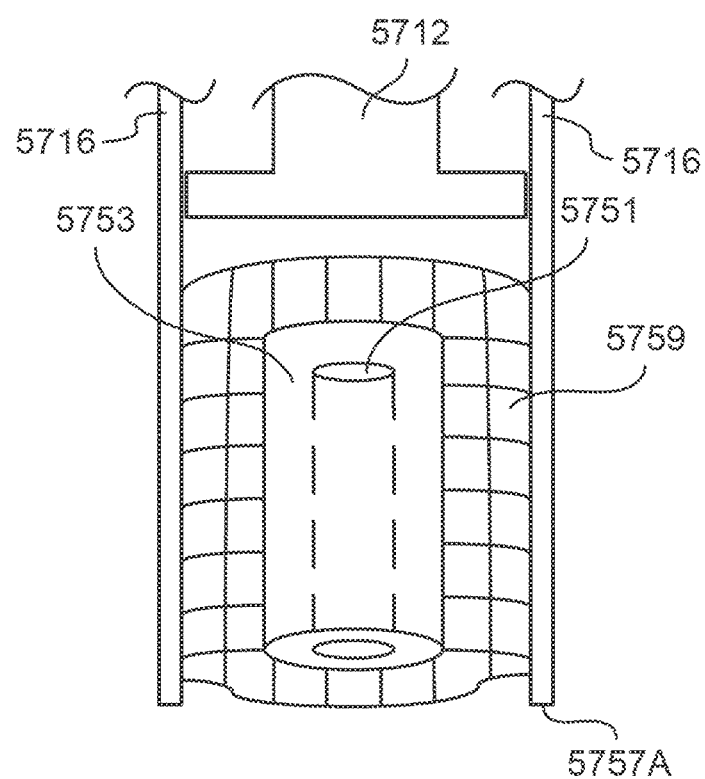
Figure 4G:
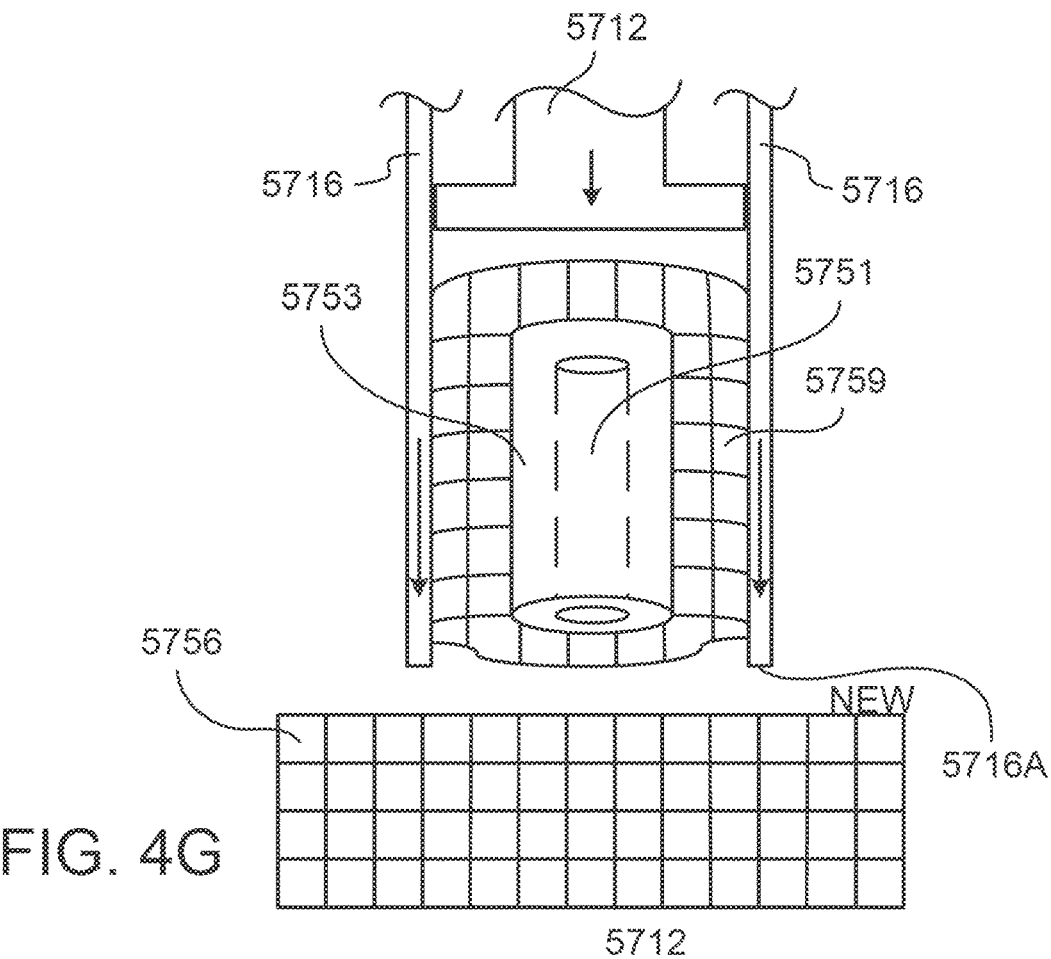
Figure 4H:
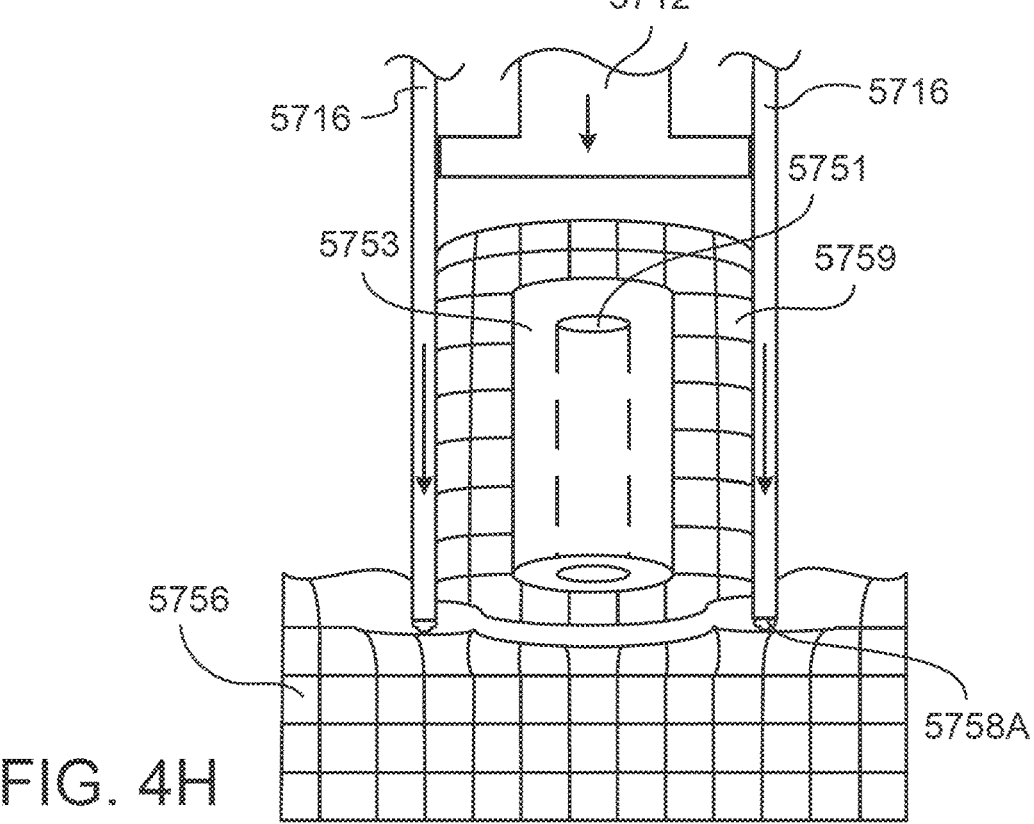
Figure 4I:
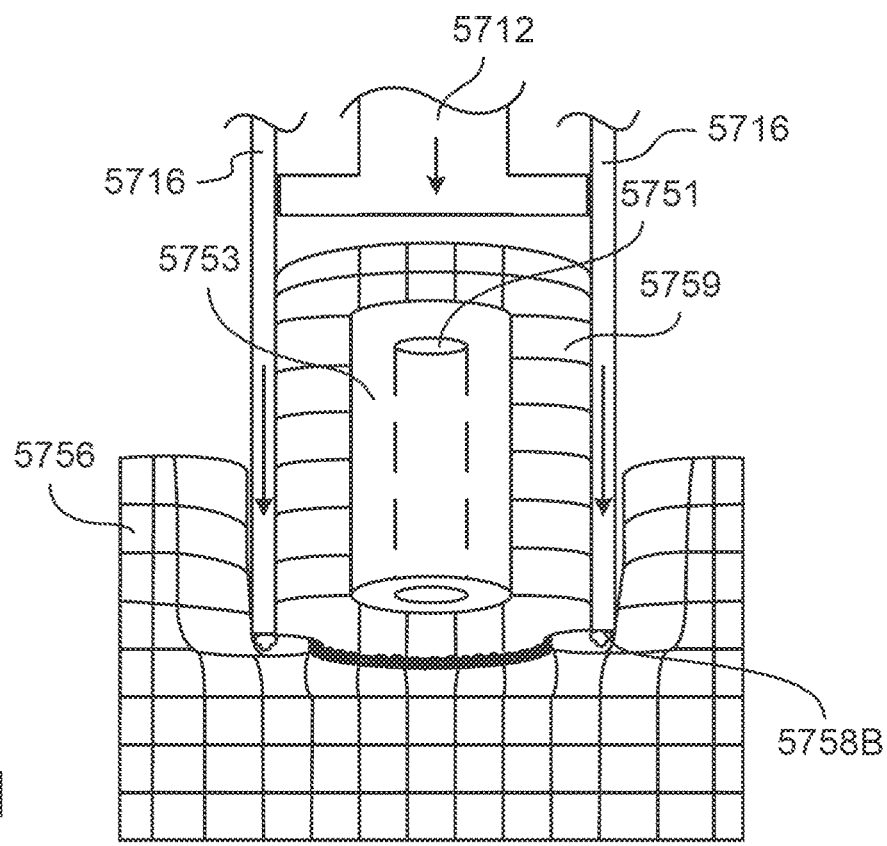
Figure 4J:
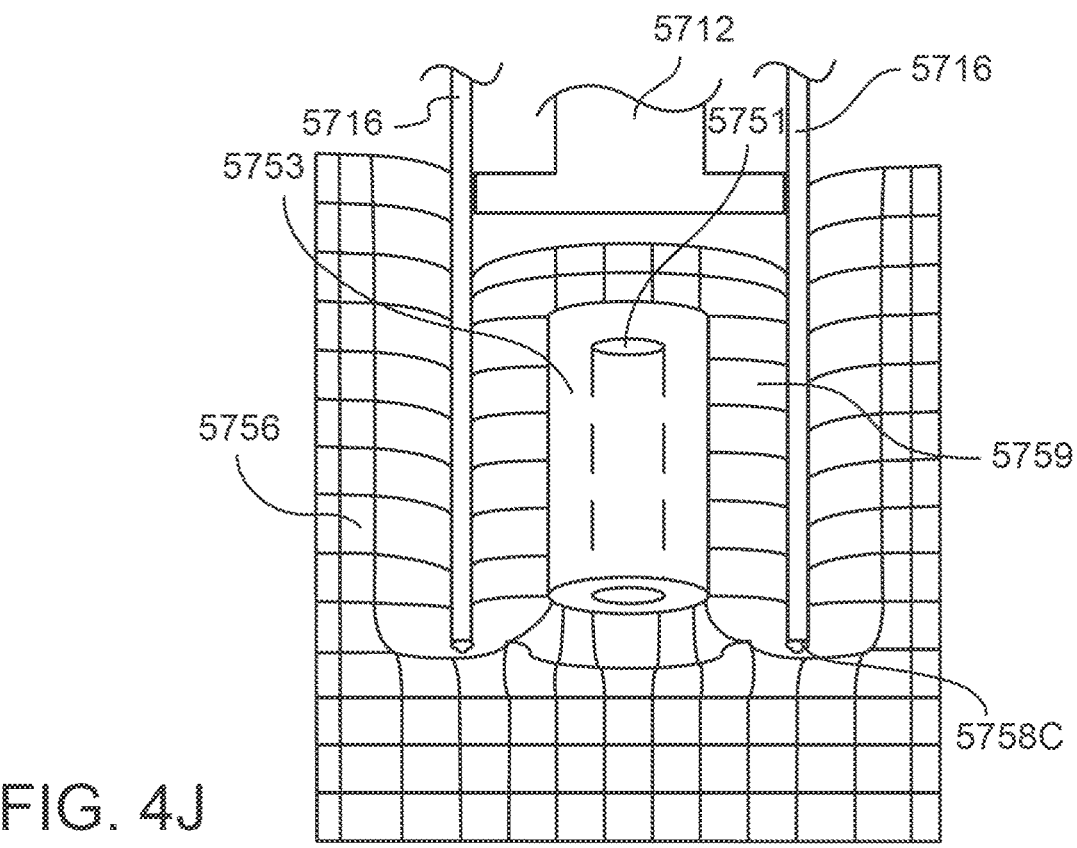
Figure 4K:
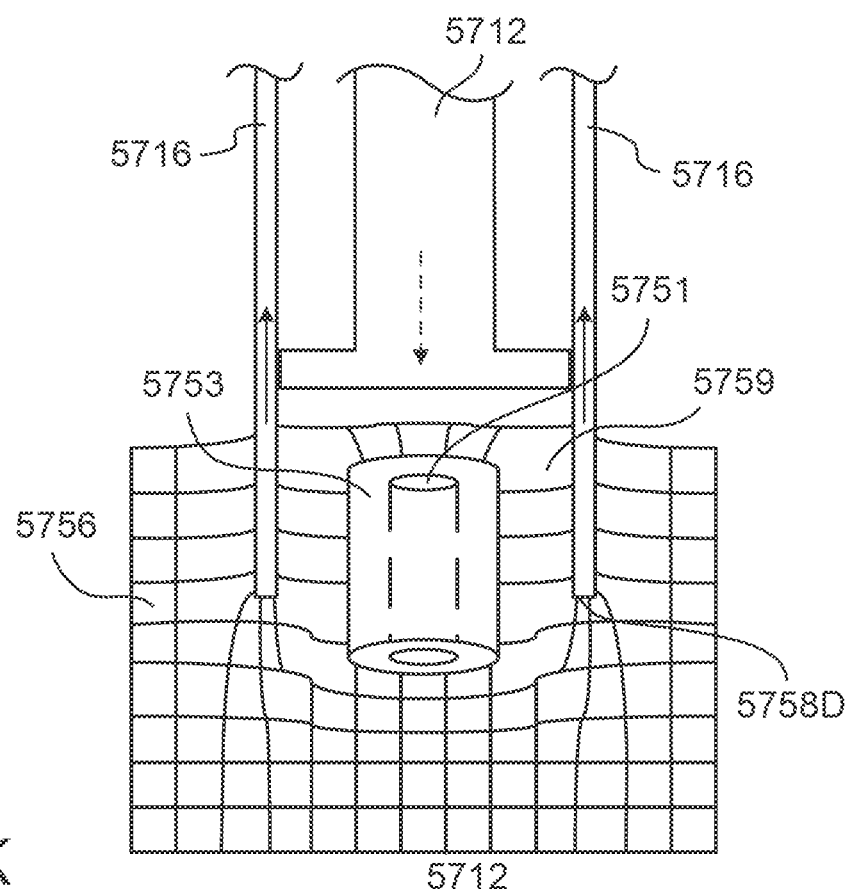
Figure 4L:
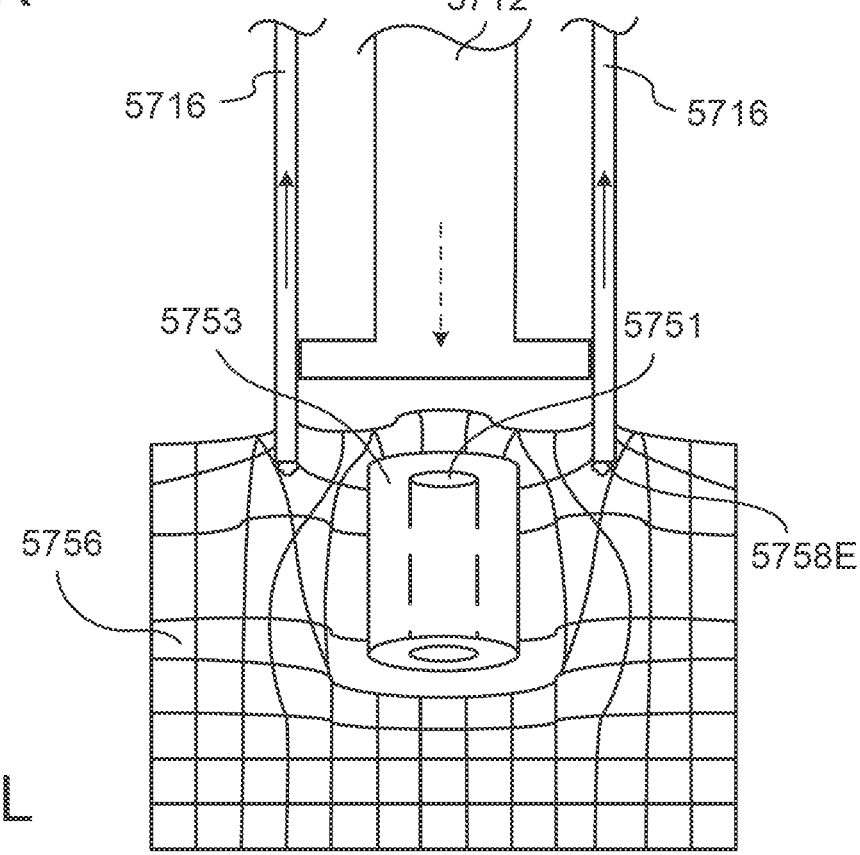
Figure 4M:
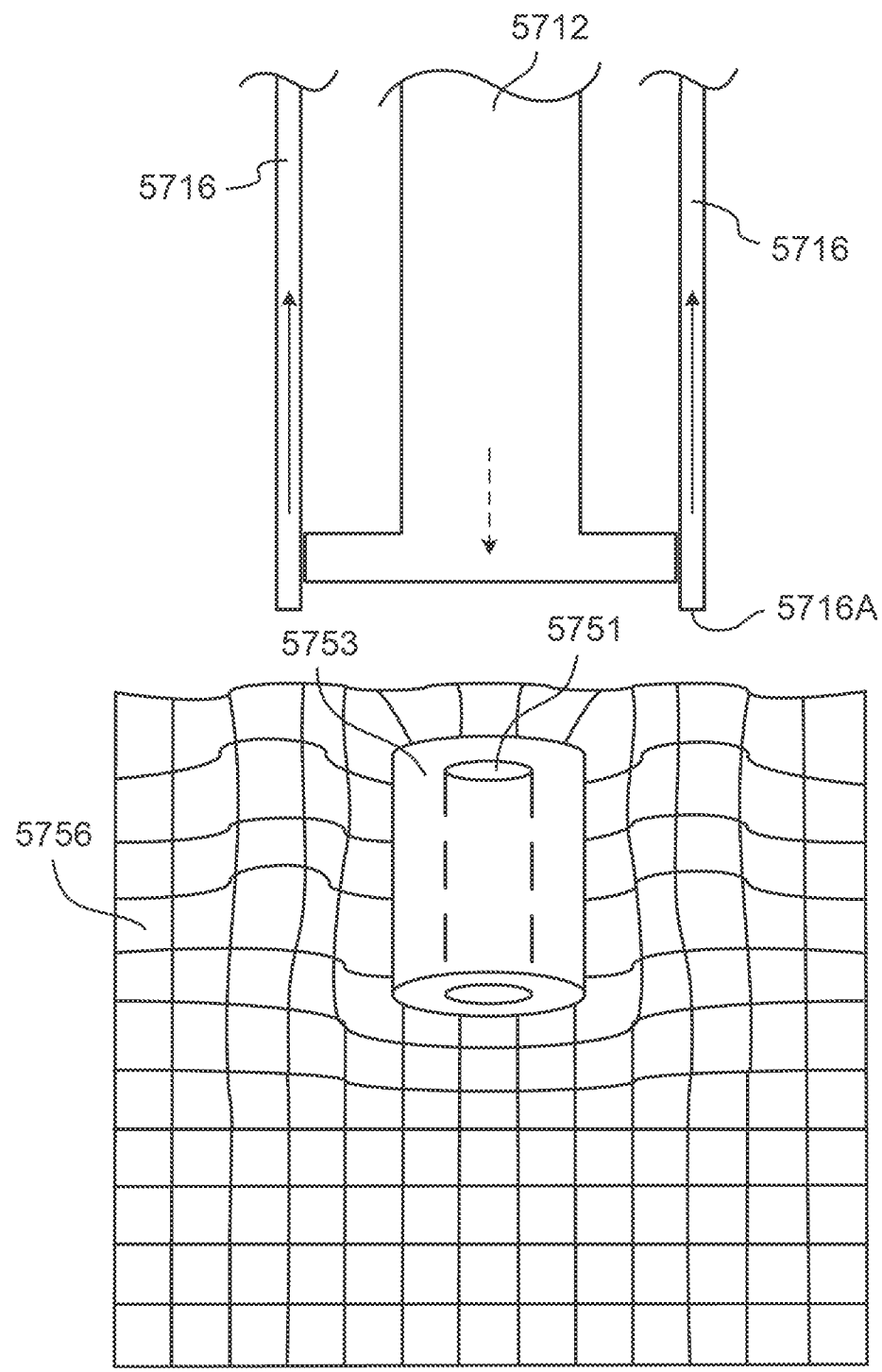

Referring now to FIGS. 4A-4M, the controller can direct the movement of needle 5716 and plunger 5712 to enter medium 5755 and surround structure 5753 and sacrificial layer 5759. If structure 5753 is a vessel, structure 5753 can include cavity 5751 that can surround medium 5755. Throughout the process of transferring structure 5753 and sacrificial layer 5759, the distance between plunger 5712 and needle end 5716A, referred to herein as distance A 5772, and the distance between plunger 5712 and sacrificial medium 5759, referred to herein as distance D 5774, can be maintained by the controller. When the process begins, distance D 5774 can take on a pre-selected value. The controller can direct the movement of needle 5716 to proceed into medium 5755 through depth 5757A (FIG. 4B) towards pre-selected depth 5757B (FIG. 4C). Meanwhile, the controller can maintain distance D 5774 at the pre-selected value by raising plunger 5712. Pre-selected depth 5757B (FIG. 4C) can extend further into medium 5755 than tissue structure 5753. At pre-selected depth 5757B (FIG. 4C), the controller can direct the movement of needle 5716 and plunger 5712 to withdraw from medium 5755 through depth 5757C (FIG. 4D) while maintaining distance D 5774. Tissue structure 5753 along with sacrificial medium 5759 accompany needle 5716 as needle 5716 is pulled away (FIG. 4E) from medium 5755 and out of the first growth area. Eventually, the controller can direct the movement of needle 5716 and plunger 5712 to a point (FIG. 4F) at which tissue structure 5753 and sacrificial medium 5759 are disconnected from medium 5755. At this point, the controller can direct the movement of transfer device 5700 towards the second growth area including second media 5756 (FIG. 4G). When transfer device 5700 arrives at the second growth area and is aligned correctly over second media 5756 (FIG. 4G), the controller can direct the movement of needle 5716 to lower needle 5716 and plunger 5712 to enter second medium 5756 (FIG. 4H) through depth 5758A (FIG. 4H). The controller can continue to direct the movement of needle 5716 to lower needle 5716 and plunger 5712 through depth 5758B (FIG. 4I) to pre-selected depth 5758C (FIG. 4J). When pre-selected depth 5758C (FIG. 4J) is reached, the controller can direct the movement of needle 5716 to withdraw needle 5716, and at the same time, the controller can direct linear actuator 5711 to depress plunger 5712 and effectively apply positive pressure to tissue structure 5753 and sacrificial medium 5759 through plunger 5712. The positive pressure can prevent tissue structure 5713 and sacrificial medium 5759 from withdrawing from second medium 5756 (FIG. 4K) when needle 5716 passes through depths 5758D (FIG. 4K) and 5758E (FIG. 4L). Eventually, needle 5716 will be completely withdrawn from second medium 5756 (FIG. 4M), leaving tissue structure 5753 and sacrificial medium 5759 behind within second medium 5756 (FIG. 4M).

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of the controller, for example, can operate on a computer having a variable number of CPUs. Other alternative computer platforms can be used.

The present embodiment is also directed to software for accomplishing the methods discussed herein, and computer readable media storing software for accomplishing these methods. The various modules described herein can be accomplished on the same CPU, or can be accomplished on a different computer. In compliance with the statute, the present embodiment has been described in language more or less specific as to structural and methodical features. It is to be understood, however, that the present embodiment is not limited to the specific features shown and described, since the means herein disclosed comprise preferred forms of putting the present embodiment into effect.

The methods of the present teachings can be, in whole or in part, implemented electronically. Signals representing actions taken by elements of the controller and the transfer system in various configurations can travel over at least one live communications network. Control and data information can be electronically executed and stored on at least one computer-readable medium. The systems can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A bioprinting system, comprising:
    a plurality of bioreactors, each having a tissue enclosure for receiving delivered tissue, the tissue enclosure including a plurality of control points, the tissue enclosure including production line mounting features;
    a multi-axis, multi-dimensional robotic printer having a delivery device operably coupled with the printer, the delivery device delivering tissue to be printed to said tissue enclosure;
    a controller controlling the motion of said robotic printer, said controller accessing a design and converting the design to coordinates that direct the robotic printer to print tissue into each tissue enclosure, the controller executing commands including:
        accessing parameters associated with the design;
    pathing of the design based on the parameters to producing coordinates of the design; and
    transferring the coordinates from the controller to the robotic printer;
        a motion controller within the robotic printer processing the coordinates including: converting coordinates to delivery points, an approach vector, an orientation vector, and at least one path;
        choosing a robot figure for each path, based on a desired robot position and range of motion;
        determining a translation data type based on the approach vector, the orientation vector, and the robot figure;
        creating at least one motion command based on the translation data type and the delivery points; and
        printing the tissue into each tissue enclosure by commanding the printer based on the at least one motion command.

2. The bioprinting system of claim 1, further comprising: a delivery device locating subsystem, including:
    a mounting plate including kinematic positioning features; and each tissue enclosure being mounted at a pre-selected orientation, each tissue enclosure including kinematic mounting features complementary with the kinematic positioning features, the kinematic mounting features matably couplable with the kinematic positioning features, the mounting features and the positioning features forcing each tissue enclosure to be mounted at the pre-selected orientation and no other orientations.

3. The bioprinting system of claim 1, wherein the motion controller comprises a sensor processor, a group processor, and a node processor, the group processor managing at least one group, the at least one group including at least one node, the at least one node associated with at least one actuator, the node processor managing the at least one actuator, the sensor processor managing at least one sensor hardware through at least one sensor driver, the sensor processor communicating the sensor data to the group processor and the node processor.

4. The bioprinting system of claim 3, wherein the motion controller comprises at least one actuator driver driving the at least one actuator, at least one hardware driver driving the at least one hardware device, and an error processor tracking errors encountered by the motion controller.

5. The bioprinting system of claim 1, the delivery device further comprising: bi-directional fluid control between the delivery device and each tissue enclosure.

6. The bioprinting system of claim 1, the delivery device further comprising:
    input means for a plurality of input materials; and
    a mixing valve receiving the plurality of input materials, the mixing valve extruding a single stream of the input materials as the printed tissue.

* * * * *